(12) United States Patent
Matthews et al.

(10) Patent No.: US 12,036,040 B2
(45) Date of Patent: Jul. 16, 2024

(54) COMPUTER-IMPLEMENTED TRAINING PROGRAMS, SUCH AS FOR IMPROVING USER PERFORMANCE

(71) Applicant: Neuropeak Pro LLC, Grand Rapids, MI (US)

(72) Inventors: Andrew David Matthews, East Grand Rapids, MI (US); Richard Warren Kuiper, Hudsonville, MI (US); Elyse White, East Grand Rapids, MI (US); Nick Bolhuis, Hudsonville, MI (US); Jason Robel, Wake Forest, NC (US); Lauro Ojeda, Ann Arbor, MI (US); David Harkey, Palm Bay, FL (US); Nora Syzmkowski, Jackson, MI (US); Noel Perkins, Lagunitas, CA (US); Grant Kruger, Saline, MI (US)

(73) Assignee: Neuropeak Pro LLC, Grand Rapids, MI (US)

( * ) Notice: Subject to any disclaimer, the term of this patent is extended or adjusted under 35 U.S.C. 154(b) by 0 days.

(21) Appl. No.: 18/345,221

(22) Filed: Jun. 30, 2023

(65) Prior Publication Data
US 2024/0065625 A1 Feb. 29, 2024

Related U.S. Application Data

(60) Provisional application No. 63/374,176, filed on Aug. 31, 2022.

(51) Int. Cl.
*A61B 5/00* (2006.01)
*A61B 5/0205* (2006.01)
(Continued)

(52) U.S. Cl.
CPC ............ *A61B 5/486* (2013.01); *A61B 5/0004* (2013.01); *A61B 5/0205* (2013.01);
(Continued)

(58) Field of Classification Search
None
See application file for complete search history.

(56) References Cited

U.S. PATENT DOCUMENTS

| 5,577,510 A | 11/1996 | Chittum et al. |
| 8,033,996 B2 | 10/2011 | Behar |

(Continued)

FOREIGN PATENT DOCUMENTS

| CN | 104665787 A | 6/2015 |
| CN | 204839484 U | 12/2015 |

(Continued)

*Primary Examiner* — Kesha Frisby
(74) *Attorney, Agent, or Firm* — Perkins Coie LLP

(57) ABSTRACT

Methods and systems for generating physiological metrics for display on a computing device are disclosed herein. In some implementations, an exemplary system comprises a torso wearable device including a wireless transmitter and a sensor, and non-transitory computer-readable media (CRM). The CRM, when executed by a computing device in communication with the wireless transmitter, can perform operations comprising: receiving the input signals representing respiration of the user; displaying a graphical user interface to the user; receiving one or more user inputs associated with a desired metric; displaying on the graphical user interface a first visualization corresponding to the desired metric; and displaying on the graphical user interface a second visualization corresponding to a physiological metric based on the input signals generated from the sensor. The second visualization can change in real time based on real time angular displacement of the sensor in response to the respiration of the user.

20 Claims, 15 Drawing Sheets

(51) Int. Cl.
*A61B 5/024* (2006.01)
*A61B 5/08* (2006.01)

(52) U.S. Cl.
CPC .......... *A61B 5/6823* (2013.01); *A61B 5/7425* (2013.01); *A61B 5/7475* (2013.01); *A61B 5/02405* (2013.01); *A61B 5/02438* (2013.01); *A61B 5/0816* (2013.01)

(56) References Cited

U.S. PATENT DOCUMENTS

| | | |
|---|---|---|
| 8,036,735 B2 | 10/2011 | Cazares et al. |
| 8,827,906 B2 | 9/2014 | Yuen et al. |
| 8,834,364 B2 | 9/2014 | Heneghan et al. |
| 9,039,614 B2 | 5/2015 | Yuen et al. |
| 9,125,630 B2 | 9/2015 | Menzel |
| 9,173,575 B2 | 11/2015 | Woodford |
| 9,675,291 B2 | 6/2017 | Braspenning et al. |
| 9,895,096 B2 | 2/2018 | Nims et al. |
| 10,052,034 B2 | 8/2018 | Braun et al. |
| 10,154,460 B1 | 12/2018 | Miller et al. |
| 10,188,345 B2 | 1/2019 | Venkatraman et al. |
| 10,463,260 B1 | 11/2019 | Davydov et al. |
| 10,543,386 B2 | 1/2020 | Sokol et al. |
| 10,631,776 B2 | 4/2020 | Annoni et al. |
| 10,980,433 B2 | 4/2021 | Persen et al. |
| 11,337,615 B2 | 5/2022 | Ahmad et al. |
| 2008/0214903 A1 | 9/2008 | Orbach |
| 2009/0024004 A1 | 1/2009 | Yang |
| 2009/0221888 A1 | 9/2009 | Wijesiriwardana |
| 2009/0281394 A1 | 11/2009 | Russell et al. |
| 2012/0277521 A1 | 11/2012 | Chamberlin |
| 2014/0073970 A1 | 3/2014 | Ashby |
| 2014/0121473 A1 | 5/2014 | Banet et al. |
| 2014/0316191 A1 | 10/2014 | de Zambotti et al. |
| 2014/0330139 A1 | 11/2014 | Banet et al. |
| 2015/0265161 A1 | 9/2015 | Hernandez et al. |
| 2016/0030809 A1 | 2/2016 | Wisbey et al. |
| 2016/0367188 A1 | 12/2016 | Malik et al. |
| 2017/0202484 A1 | 6/2017 | Al-Shaery et al. |
| 2017/0251967 A1 | 9/2017 | Premsukh |
| 2017/0347894 A1 | 12/2017 | Bhushan et al. |
| 2017/0347899 A1 | 12/2017 | Bhushan et al. |
| 2018/0249947 A1 | 9/2018 | Seegmiller Maudlin |
| 2018/0358119 A1 | 12/2018 | Bhushan et al. |
| 2021/0204867 A1* | 7/2021 | Toth ..................... A61B 5/0002 |
| 2021/0401314 A1 | 12/2021 | Pho et al. |
| 2022/0005580 A1 | 1/2022 | Pavlov et al. |
| 2022/0175309 A1 | 6/2022 | Vardas et al. |
| 2022/0249021 A1 | 8/2022 | Ahmad et al. |
| 2022/0360913 A1 | 11/2022 | Stapt et al. |

FOREIGN PATENT DOCUMENTS

| | | |
|---|---|---|
| CN | 107334460 A | 11/2017 |
| CN | 112036966 A | 12/2020 |
| CN | 212521748 U | 2/2021 |
| KR | 20100049905 A | 5/2010 |
| KR | 20100081717 A | 7/2010 |
| KR | 20120045661 A | 5/2012 |
| KR | 20120045664 A | 5/2012 |
| KR | 20120066868 A | 6/2012 |
| KR | 20150057429 A | 5/2015 |
| KR | 20180099030 A | 9/2018 |
| KR | 20190091880 A | 8/2019 |
| KR | 20200066204 A | 6/2020 |
| WO | 2009138923 A1 | 11/2009 |
| WO | 2010105034 A2 | 9/2010 |
| WO | 2015171667 A1 | 11/2015 |
| WO | 2016119654 A1 | 8/2016 |
| WO | 2016119657 A1 | 8/2016 |
| WO | 2016119665 A1 | 8/2016 |
| WO | 2016181148 A2 | 11/2016 |
| WO | 2018219030 A1 | 12/2018 |

* cited by examiner

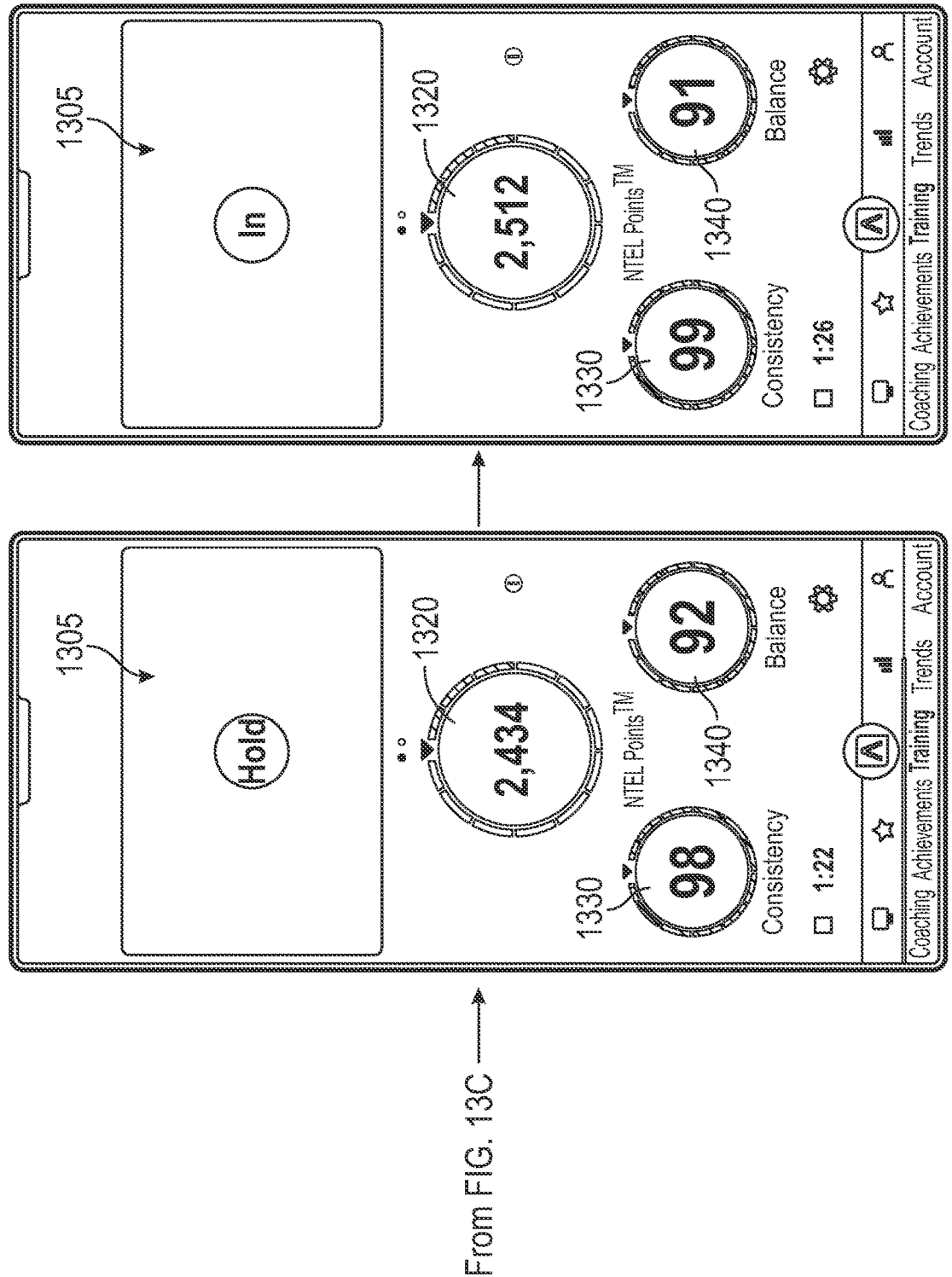

COMPUTER-IMPLEMENTED TRAINING PROGRAMS, SUCH AS FOR IMPROVING USER PERFORMANCE

CROSS-REFERENCE TO RELATED APPLICATIONS

The present application claims the benefit of priority to U.S. Provisional Patent Application No. 63/374,176, filed Aug. 31, 2022, the disclosure of which is incorporated herein by reference in its entirety.

TECHNICAL FIELD

This present disclosure relates to computer-implemented training programs for improving user performance or otherwise providing user feedback to improve a user's condition, and associated systems, devices, and methods. Particular implementations of the present disclosure relate to training systems and software for improving breathing, heart rate variability, and brain performance.

BACKGROUND

Athletes and other individuals that operate under high-pressure conditions and/or competitive environments often experience high anxiety and stress, which can lead to autonomic responses (e.g., fight or flight responses) including increased heart rate and/or fast and shallow breathing. As a result of these physiological responses, individuals can easily lose focus and perform at less than peak levels. Training for such individuals is essential in order to teach the mind and body to prepare for and cope with these physiological responses when high-pressure conditions arise. However, conventional trainers, coaches, techniques, and training devices are often not effective due to, e.g., their inability to process raw physiological data from the user in real time. Moreover, conventional training devices and techniques lack the ability to overlay or map current breathing metrics of the user to the desired respiration metric. As such, conventional devices are unable to effectively train users to breathe in a way that more efficiently supports the autonomic nervous system or physiology of the user. Therefore, a need exists to develop improved methods and/or programs to enable users to better respond to stressful conditions and perform in high-pressure environments.

BRIEF DESCRIPTION OF THE DRAWINGS

Features, aspects, and advantages of the presently disclosed technology may be better understood with regard to the following drawings.

FIGS. 13A-13E are illustrations of a user interface including continuously updated metrics and dynamic breathing instructions provided to users, in accordance with implementations of the present technology.

Figure 1:
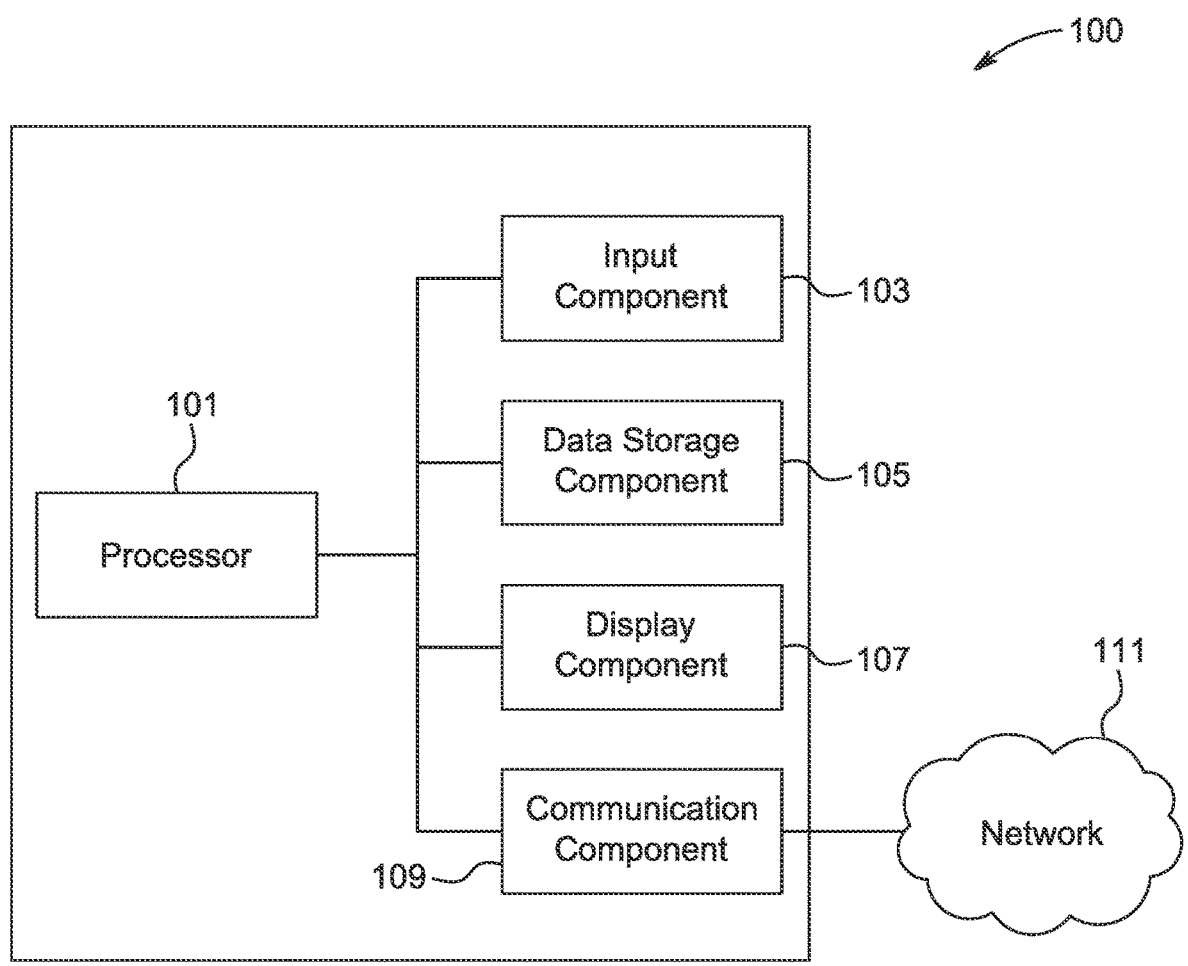
FIG. 1 is a schematic block diagram of a computing device, in accordance with implementations of the present technology.

A person skilled in the relevant art will understand that the features shown in the drawings are for purposes of illustrations, and variations, including different and/or additional features and arrangements thereof, are possible.

DETAILED DESCRIPTION

I. Overview

Implementations of the present disclosure relate to generating a desired respiration signal or metric based on user inputs, and processing raw data signals received from a device sensor to produce physiological metrics of the user. One or more of the physiological metrics can be overlayed onto the desired respiration metric in a manner that trains the user to modulate their breathing, and can thereby enable the user to better respond to stressful conditions and perform in high-pressure environments.

As noted above, athletes and other individuals that operate under high-pressure conditions that lead to autonomic responses (e.g., fight or flight responses), and can easily lose focus and perform at less than peak levels. Training for such individuals is essential in order to teach the mind and body to prepare for and cope with these physiological responses when high-pressure conditions arise. However, conventional trainers, coaches, techniques, and training devices are often not effective due to, e.g., their inability to process raw physiological data from the user in real time.

These challenges indicate a fundamental technological problem with the user experience regarding the processing of raw data signals associated with a user's breathing and physiology, and the ability to effectively display processed data or metrics to the user via visualizations of the processed raw signals that can be continuously updated (e.g., in real time). Because this problem specifically arises in the realm of computerized networks, a solution rooted in computer technology to overcome these issues is needed.

Implementations of the present disclosure ("the system") attempt to address the above-described issues, e.g., by receiving input signals for or from the user that correspond to breathing and/or heart rate variability, and processing those input signals to produce metrics that are displayed for the user and updated in real time. For example, implementations of the present disclosure include systems, methods, and/or computer-readable media for receiving one or more input signals from a device sensor operably coupled to a user, and receiving user inputs to produce a desired respiration metric. The one or more input signals are processed to produce metrics related to measuring respiration (e.g., physical respiration patterns), heart rate variability, and other biomarkers related to the body's stress responses (e.g., respiration consistency and other performance metrics). Visualizations of the desired respiration metric and one or more of the produced metrics are displayed to the user via a computing device, and in some implementations updated in real time. As an example, the displayed visualizations can simultaneously include (i) the respiration metric corresponding to the actual inhalation/exhalation of the user, and (ii) the desired respiration metric. In such implementations, shift and/or scale coefficients generated in part from the received user inputs can enable the respiration metric to be mapped or overlayed over (e.g., aligned with) the desired respiration metric, thereby enabling the user to visually monitor, measure, and modulate the difference between actual and desired respiration. In doing so, implementations of the present technology enable users to train their breathing in real-time, and as a result improve their breathing, heart rate variability, and/or mental performance.

The system can also produce performance metrics from the input signals that provide measurable analytics to the user to improve breathing and heart rate variability. For example, a performance metric can be generated based on an average of the consistency metrics and a low frequency percentage metric (sometimes referred to as "balance"). The low frequency percentage metric can be generated based on heart rate data of the user, or more specifically by filtering the heart rate data and utilizing a Fourier transform (e.g., a fast Fourier transform) to generate power values that have frequencies within a predetermined frequency range. As explained in more detail elsewhere herein, the consistency metric can indicate the repeatability of a user's inhalation/exhalation over time and the low frequency percentage metric can indicate an amount of sympathetic activity of the user, which is associated with desired increased heart rate variability. As such, the generated performance metric, which is based on the consistency and low frequency percentage metrics, can serve as a measurable value for the user to gauge the consistency and quality of their training over time.

In addition to the performance metric itself, the system can also produce performance scores and performance points that track a user's training, improvement, and quality of breathing technique over time. By generating these scores and points, users can compare their performance to those of peers and thus compete against one other. As the performance scores and points are linked to the amount and quality of training, as well as the consistency of training over time, users of the implementations disclosed herein are motivated to spend more time training and improving the quality of their breathing over time.

The system can be utilized in markets/fields of use in which users operate under high-pressure conditions and/or competitive environments, such as sports. Additionally, the present technology can be utilized to aid substance cessation (e.g., for smoking, drinking, prohibited substances, gambling, etc.), as well as for meditation/mental training, sleep quality, and yoga.

In the Figures, identical reference numbers identify generally similar, and/or identical, elements. Many of the details, dimensions, and other features shown in the Figures are merely illustrative of particular implementations of the disclosed technology. Accordingly, other implementations can have other details, dimensions, and features without departing from the spirit or scope of the disclosure. In addition, those of ordinary skill in the art will appreciate that further implementations of the various disclosed technologies can be practiced without several of the details described below.

II. System Architecture of Computer-implemented Training Programs for Improving User Performance FIGS. 1 and 2 and the following discussion provide a brief, general description of suitable computing environments in which aspects of the present technology can be implemented. Although not required, aspects of the system will be described in the general context of computer-executable instructions, such as routines executed by a general-purpose computer, e.g., a server or personal computer (e.g., a cellular or mobile device). Those skilled in the relevant art will appreciate that the present technology can be practiced with other computer system configurations, including Internet appliances, hand-held devices, wearable computers, multi-processor systems, microprocessor-based or programmable consumer electronics, set-top boxes, mini-computers, mainframe computers, and the like. The present technology can be embodied in a special purpose computer or data processor that is specifically programmed, configured, or constructed to perform one or more of the computer-executable instructions explained in detail below. In some implementations, the disclosed functionality may be implemented by instructions encoded in a non-transitory computer-readable storage medium.

The present technology can also be practiced in distributed computing environments, where tasks or modules are performed by remote processing devices, which are linked through a communications network, such as a Local Area Network ("LAN"), Wide Area Network ("WAN") or the Internet. In a distributed computing environment, program modules or sub-routines may be located in both local and remote memory storage devices. Aspects of the present technology described below can be stored or distributed on computer-readable media, stored as firmware in chips (e.g., Electrically-Erasable Programmable Read-Only Memory chips, EEPROM chips), as well as distributed electronically over the Internet or over other networks (e.g., wireless networks). Those skilled in the relevant art will recognize that portions of the present technology can reside external to a mobile device (e.g., on a server computer or a sensor), while corresponding portions reside on a mobile device. Data structures and transmission of data particular to aspects of the present technology are also encompassed within the scope of the present technology.

FIG. 1 is a schematic block diagram illustrating components of a computing device 100, such as a smartphone, desktop computer, tablet computer, phablet, laptop, wearable computer, etc., in which the interface for visualizations of physiological (e.g., breathing-related and/or heart/related) metrics can be generated and displayed. As shown in FIG. 1, the computing device 100 includes a processor 101, an input component 103, a data storage component 105, a display component 107, and a communication component 109. The processor 101 is configured to couple with and control other components in the computing device 100. The computing device 100 can communicate with other systems (e.g., web servers or other devices) through the communication component 109 via a network 111. In some implementations, the computing device 100 can communicate with an output device (e.g., printers, speakers, tactile output devices, etc.) through the communication component 109. Network 111 can be any private or public network, such as the Internet, a corporate intranet, a wireless communication network (e.g., Wi-Fi, cellular, Bluetooth®, Zigbee, etc.) or a wired communication network.

The input component 103 is configured to receive an input (e.g., an instruction or a command) from a device user. The input can include user specific data, such as weight, height, gender, demographics, etc. The input component 103 can include a touch pad, a touchscreen, a microphone, a keyboard, a mouse, a camera, a joystick, a pen, a game pad, a scanner, and/or the like. The data storage component 105 can include any type of computer-readable media that can store data accessible to the processor 101. In some implementations, the data storage component 105 can include random-access memories (RAMs), read-only memories (ROMs), flash memory cards, magnetic hard drives, optical disc drives, digital video discs (DVDs), cartridges, smart cards, etc.

The display component 107 is configured to display information to the user, e.g., via a mobile device. In some implementations, the display component 107 can include flat panel displays such as liquid crystal displays (LCDs), light emission diode (LED) displays, plasma display panels (PDPs), electro-luminescence displays (ELDs), vacuum fluorescence displays (VPDs), field emission displays (FEDs), organic light emission diode (OLED) displays, surface conduction electron emitter displays (SEDs), or carbon nano-tube (CNT) displays.

Figure 2:
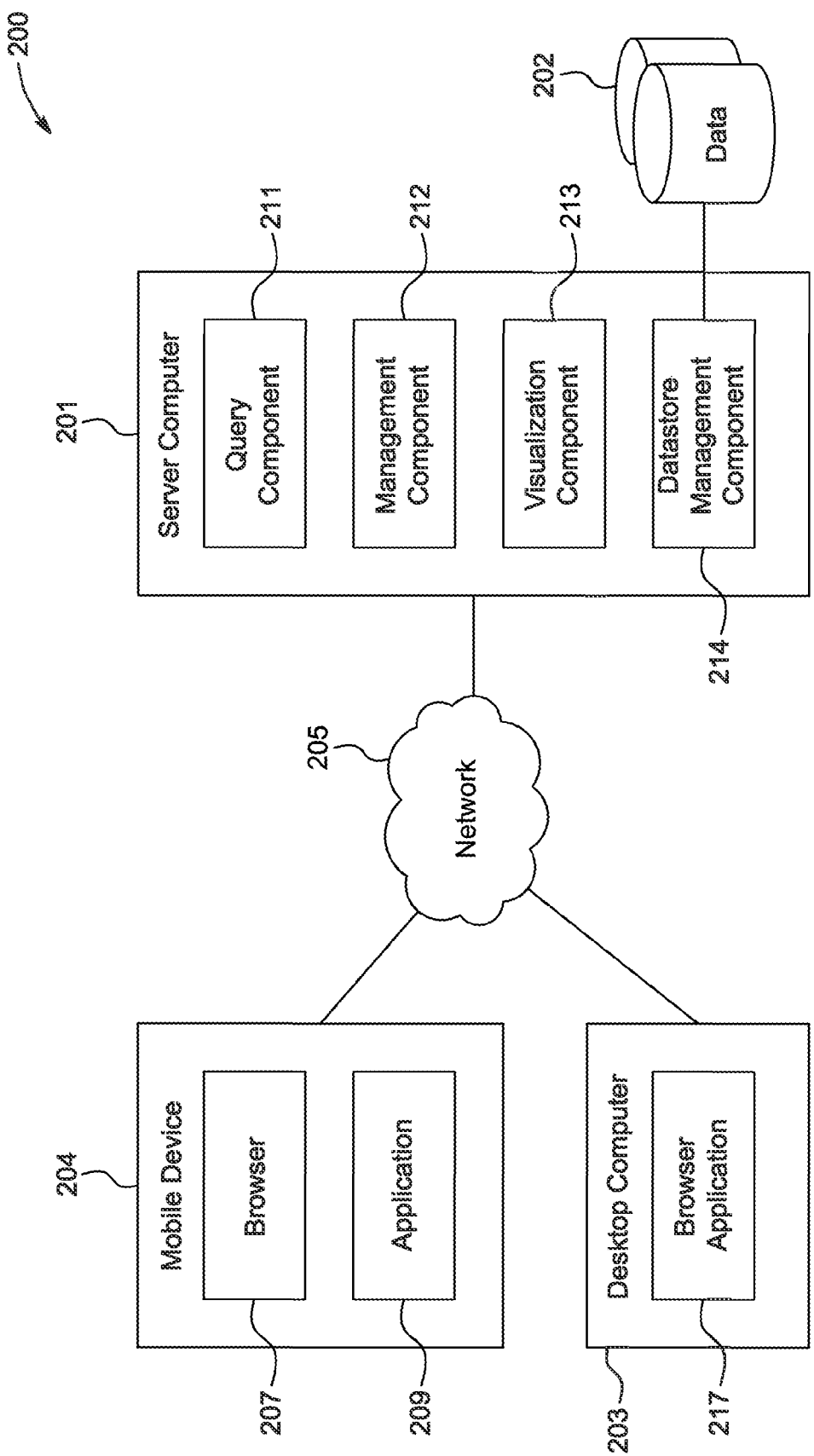
FIG. 2 is a schematic block diagram illustrating a suitable environment in which the disclosed system can operate, in accordance with implementations of the present technology.

FIG. 2 is a schematic block diagram of an environment 200 in which the system for generating an interface for displaying visualizations of physiological metrics of the user can operate. The environment 200 can include one or more server computers 201 that access data stores 202 containing information on a plurality of unique items. The server computers 201 communicate with computing devices 100 via a network 205. The computing devices 100 may send search queries to the server computers 201 pertaining to the unique items. The search queries are processed by the server computers 201 against the data in the data stores 202. The server computers 201 may retrieve, analyze, and/or format (e.g., in datasets) unique item information that is responsive to the received search queries. The server computer 201 transmits data responsive to the search queries to a requesting computing device 100 through the network 205. The network 205 can include the Internet, an intranet, a wireless communication, or a wired communication.

The server computer 201 includes a query processing component 211, a management component 212, a visualization component 213, and a database management component 214. The query component 211 is configured to perform query processing and analysis, e.g., of physiological data to produce one or more metrics (e.g., respiration, consistency, heart rate variability, performance, etc.). The management component 212 is configured to handle creation, display and/or routing of suitable information, e.g., amongst different layers or in the form of web pages. The visualization component 213 is configured to serve visualizations as described herein in a manner that generates a display of an item or metric. The visualization component 213 may be separate from, or incorporated within, the management component 212. The database management component 214 is configured to manage access to and maintenance of data stores 202. The server computer 201 can employ security measures (e.g., firewall systems, secure socket layers (SSL), password protection schemes, encryption, and/or the like) to inhibit malicious attacks and to preserve integrity of the information stored in the data stores 202.

The computing device 100 may include one or more programs that submit queries to the server computers and receive responsive results. For example, a browser application 207 on a mobile device 204 is configured to access and exchange data with the server computer 201 through the network 205. Results of data queries may be displayed in a browser (e.g., Firefox, Chrome, Internet Explorer, Safari, etc.) of the mobile device 204 for viewing by the device user. Similarly, a browser application 217 on a desktop computer 203 is configured to access and exchange data with the server computer 201 through the network 205, and the results of the data queries may be displayed in the browser for review by the device user. As another example, a dedicated application 209 on the mobile device 204 is configured to display or present received information to a mobile device user via the application. Data may be received from the server computer 201, e.g., via an application programming interface (API), and the received data formatted for display by the application on the computing device 100. The server computer 201 and the computing device 100 can include other programs or modules such as an operating system, one or more productivity application programs (e.g., word processing or spread sheet applications), and the like.

Figure 3A:
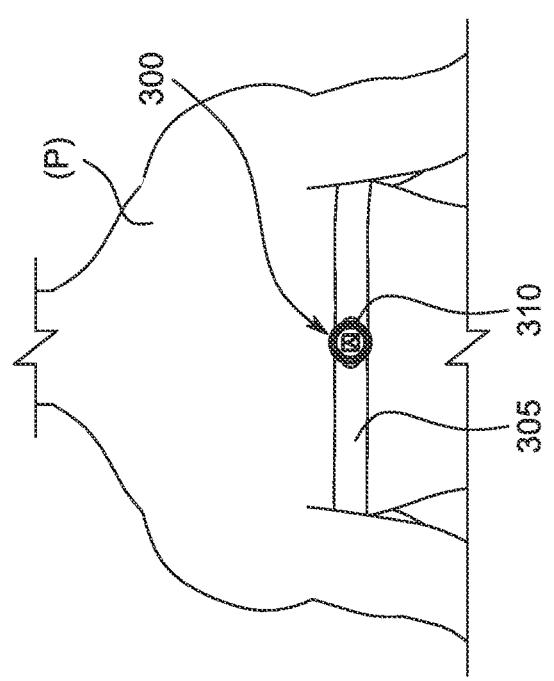
FIG. 3A is a front view of a system including a belt and a sensor being worn by a user, in accordance with implementations of the present technology.
Figure 3B:
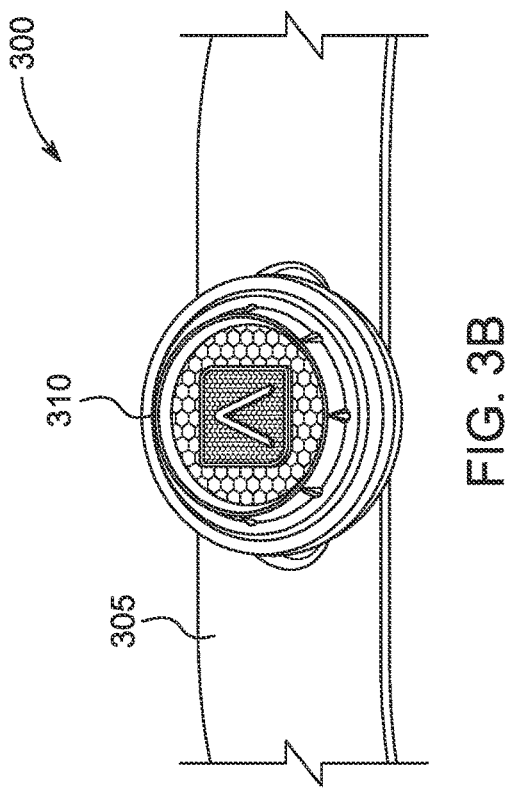
FIG. 3B is an isometric view of the system of FIG. 3A.
Figure 3C:
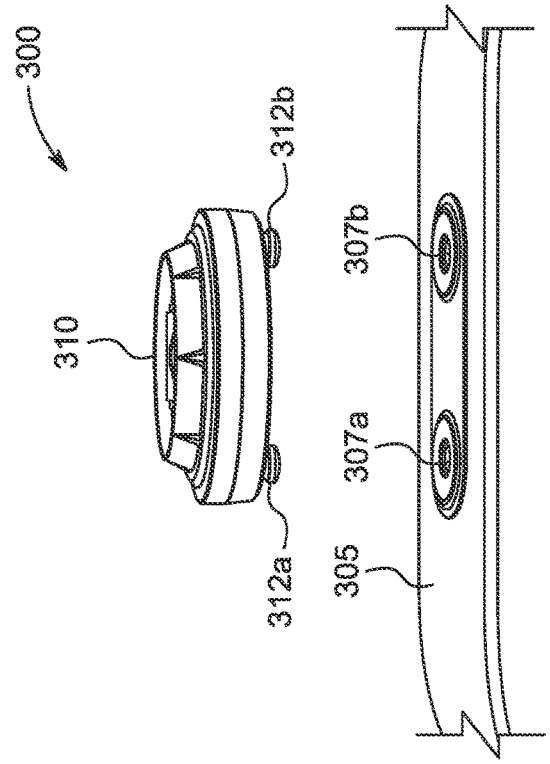
FIG. 3C is a side view of the system of FIG. 3A.

III. Computer-Implemented Training Programs for Improving User Performance, and Associated Systems, Devices, and Methods FIG. 3A-3C are various views of a system 300 including a belt 305 (e.g., a strap) and a sensor 310 detachably coupled to the belt 305, with FIG. 3A being a front view of the system 300 being worn by a user/person (P), FIG. 3B being an isometric view of the system 300, and FIG. 3C being a side view of the system 300. Referring to FIGS. 3A-3C together, the belt 305 can be worn across the torso (e.g., chest or stomach) of a user, such that the sensor 310 is positioned at the base of (e.g., two fingers below) the user's sternum (as shown in FIG. 3A) and moves toward and/or away from the user's chest with each respective inhale and exhale. For example, in some implementations the sensor 310 moves in an angular direction in response to inhalation and/or exhalation, such that a pitch of the sensor 310 relative to a base position corresponds to an amount of inhalation/exhalation and/or expansion/contraction of the diaphragmatic region.

The sensor 310 and/or the belt 305 can include an accelerometer, a gyroscope, a strain gauge/load cell, a source of light, and other hardware that individually or together measures and/or enables measurement of "raw" physiological data from the user. For example, as the user inhales and exhales, the sensor 310 can be angularly displaced from a base position, and the amount of angular displacement can be provided (e.g., on a continuous or periodic basis) to an external device or system for processing. In some implementations, the sensor 310 measures (e.g., via the gyroscope and accelerometer) respiration amplitude and frequency using kinematics. The raw data generated via the sensor 310 can be used to determine numerous metrics, including heart rate, respiration (e.g., respiration rate), R-R interval, volume displacement (e.g., during inhalation and/or exhalation), heart rate variability, consistency, symmetry, and/or coherence, as explained elsewhere herein (e.g., with reference to FIG. 4). In some implementations, the sensor 310 and/or the belt 305 correspond in whole or in part to the respective Movesense sensor and belt designed by Movesense of Vantaa, Finland.

As shown in FIG. 3C, the sensor 310 can include coupler portions 312a/b, and the belt 305 can include receiver portions 307a/b configured to receive the coupler portions 312a/b, thereby attaching the sensor 310 to the belt 305. In some implementations, the coupler portions 312a/b and receiver portions 307a/b are made from conductive materials and thereby electrically couple the sensor 310 to the belt 305, which may be electrically coupled to the user. In doing so, the sensor 310, and system 300 generally, can obtain electrical signals from the user.

A person of ordinary skill in the art will appreciate the sensor 310 and belt 305 shown in FIGS. 3A-3C represent just one implementation of the system 300. In other implementations, the sensor 310 is one of multiple sensors (e.g., two sensors, five sensors, etc.), and individual sensors may be configured to obtain specific data from a single source. For example, in such implementations a first sensor is configured to obtain heart rate or R-R interval data, a second sensor is configured to obtain air displacement or diaphragmatic contraction and expansion, and so on and so forth. Additionally or alternatively, the sensor 310 can be operably coupled to the user at areas other than the torso, such as the wrist, leg, arm, neck, heart, ear, etc. A person or ordinary skill in the art will also appreciate that the system 300 can include other components not shown in FIGS. 3A-3C, such as a wireless transmitter coupled to the sensor and configured to transmit signals from the sensor to an external computing device.

Figure 4:
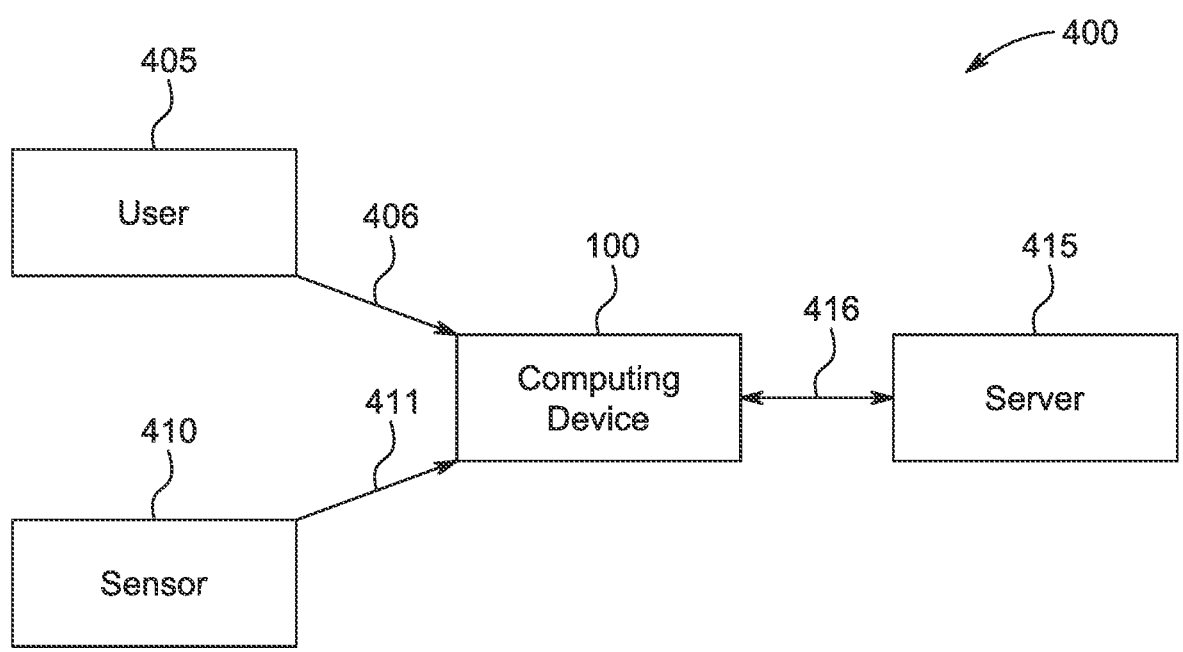
FIG. 4 is a schematic block diagram of a system illustrating data communication to and from the computing device of FIG. 1, in accordance with implementations of the present technology.

FIG. 4 is a schematic block diagram of a system 400 illustrating data communication to and from the computing device 100 of FIG. 1, in accordance with the system. As shown in FIG. 4, the computing device 100 can be configured to receive user inputs 406 from a user 405, and one or more input signals 411 ("input signal(s) 411") from a sensor 410. The sensor 410 can correspond to the sensor 310 of FIGS. 3A-3C or other sensors that can provide similar functionality (e.g., the ability to provide raw physiological data of the user). The sensor can be wirelessly connected to computing device 100, or physically connected to the computing device 100. Additionally, the computing device 100 can be configured to process the input signal(s) 411 to produce metrics 416, and/or direct the input signal(s) 411 to a remote server 415 to produce the metrics 416.

The user inputs 406 can include user-specific data (e.g., age, weight, height, build, and/or gender), respiration settings, and/or physiologic data obtained from the user during a training session (e.g., as explained with reference to FIGS. 6A-6F) in which the user's breathing patterns (e.g., inhalation, exhalation, and/or diaphragmatic expansion and contraction, etc.) are monitored. The respiration settings can include parameters or times that correspond to inhale, hold after inhale, exhale, and/or hold after exhale. The combination of these individual respiration settings can produce a desired respiration metric or data for the user (e.g., an ideal metric or data; sometimes referred to herein "pacer data" or a "pacer signal"). In some implementations, the desired data or signal is obtained via breathing patterns of the user obtained during a training session. For example, during the training session, the user can be instructed to sequentially inhale, hold, exhale, and hold (and afterward repeat) for a predetermined period of time (e.g., 1-10 minutes or longer), as set by the system or the user. In addition to the desired signal, other coefficients (e.g., shift and scale coefficients) can be generated based on the user inputs and be used to alter visualizations or the display of one or more of the metrics 416.

The input signal(s) 411 received from the sensor 410 can include the raw physiological data, e.g., as described with reference to FIGS. 3A-3C. As such, the raw physiological data can include heart rate or R-R interval of the user, as well as an angular displacement of the sensor, which is used to generate an amount of air displaced during inhalation and/or exhalation or a relative measurement of physical movement of the abdomen area. The amount of air displaced can correlate to inhalation or exhalation, and the values corresponding to the inhale, exhale, and hold values can produce reference points for a curve that models an nth order (e.g., second order) polynomial. Such a curve is displayed to the user via a display of the computing device 100, and can be updated in real time as current input signals are received. In some implementations, the displayed curve corresponds to values that are a continuously updated rolling average (e.g., of the previous five seconds, 10 seconds, or 30 seconds of measurements). The inhale, exhale, and hold values can be obtained continuously or periodically (e.g., at least once every 100 milliseconds, every second, every five seconds, etc.).

The metrics 416 can be generated from the input signal(s) 411 received from the sensor 410 and, in some implementations, the user inputs 406. For example, the metrics 416 can be generated based predominantly on the input signal(s) 111, but be based in part on or altered by the user inputs 406 (e.g., the data obtained during the training session described above). The generated metrics 416 can include respiration volume, heart rate variability (HRV) (e.g., high frequency HRV, low frequency HRV, and very low frequency HRV), consistency, performance (sometimes referred to herein as "NTEL"), symmetry, and coherence. These metrics can be generated simultaneously and be updated in real time, such that each can be displayed to the user via the computing device 100 simultaneously, e.g., as a value, a visualization, or both. For example, multiple metrics can be overlayed on a single display with one another and other signals (e.g., the desired respiration signal).

The respiration metric value is generated based on the displacement input signal, as well as the shift and scale coefficients, which can be generated from the user inputs or data obtained during the user's training session. The respiration metric generally corresponds to the amount of air inhaled/exhaled for a particular breath, increasing in value during inhalation to a maximum value and decreasing in value during exhalation to a minimum value. The respiration metric value and other metric values disclosed herein (e.g., the HRV metric value, the consistency metric value, etc.) can be adjusted based on the shift and scale coefficients, which can align the respiration metric (e.g., along an x-axis and/or a y-axis) with a corresponding value of the desired respiration signal. For example, in some implementations the shift coefficient adjusts (e.g., along a y-axis) the height or amplitude of the inhalation/exhalation such that the height or amplitude are aligned or approximately aligned with those of the desired respiration signal. Stated differently, the shift coefficient can indicate how much to alter (e.g., add to or subtract from) the respiration metric before it is displayed to the user, and the scale coefficient can indicate how much to alter (e.g., shrink or grow) the respiration metric before it is displayed to the user.

The HRV metric value is generated based on the heart rate input signal. In some implementations, the HRV metric value is generated by processing the heart rate input signal using a three-point median filter, and then creating buffered data over a predetermined rolling period of time (e.g., the previous 2 minutes, 3 minutes, 4 minutes, etc.). In some implementations, the buffered data captured over the period of time undergoes a zero-mean shift and utilizes a Fourier transform (e.g., a chirp Z-transform and/or Bluestein's algorithm) to produce "power" values at different frequencies or frequency ranges of the HRV spectrum. The power values generally correspond to the units of electrical activity during breathing and fit into one of the three frequency ranges, which include (i) a high frequency (HF) range, e.g., 0.4-0.15 Hertz (Hz) (or 2.5-6.67 seconds (s)), (ii) a low frequency (LF) range (also referred to herein as "balance"), e.g., 0.15-0.04 Hz (or 6.67-25 s), and (iii) a very low frequency (VLF) range, e.g., 0.04-0.016 Hz (or 25-62.5 s). The HRV metric value for each frequency range can correspond to the percentage each frequency range represents of the combined three frequency ranges. For example, an HRV metric value for the LF range of 30% indicates that 30% of the HRV metric values calculated over the predetermined rolling period of time were within the LF range. The frequency ranges, or more particularly the proportion of the HRV metric values that fall within a particular frequency range can reflect particular levels of activity and serve as an indication of desirable progress for the user over time. For example, the LF range can be used as an indication of sympathetic activity, with a higher proportion being associated with more sympathetic activity, which is generally desired. The individual frequency ranges can be subsequently utilized to generate other metrics and/or displays.

The consistency metric value is based on the difference in respiration for multiple breaths or inhalations/exhalations of the user. For example, in some implementations the consistency metric value is based on a respiration rate (e.g., the number or average number of breaths per minute the user takes) and a displacement volume metric (e.g., a degree to which the abdomen is expanding/contracting with each breath). The consistency metric value can be weighted equally by the respiration rate and the displacement volume metric (e.g., be weighted 50% by the respirate rate and 50% by the displacement volume metric), or be weighted more heavily by one of the respiration rate of displacement volume metric. The consistency metric value can be between 0-100, with a higher value corresponding to more consistent breathing between multiple breaths and a lower value corresponding to less consistent breathing between multiple breaths. For example, a user having low variability for respiration volumes of multiple breaths will have a higher consistency metric value than a user having high variability for respiration volumes. The consistency metric value can be subsequently utilized to generate other metrics and/or displays.

The performance metric (sometimes referred to herein as the "NTEL Metric") can be based on the consistency metric and the HRV metric. For example, in some implementations the performance metric value is an average of the consistency metric value and the HRV metric value for the LF range (i.e., the sum of the consistency metric value and the HRV metric value for the LF range multiplied by 0.5). As such, the performance metric can provide the user with a single metric that incorporates both the variability of the user's respiration and the proportion of sympathetic activity, and thus enable the user to gauge the consistency and quality of the training over time.

The performance metric can be used to generate a performance score (sometimes referred to herein as the "NTEL Score"), which can be based on the performance metric as well as on the time spent training over a previous period of time (e.g., seven days). In some implementations, the performance score is based on (i) the amount of minutes that a user trained beyond a minimum total time threshold (e.g., 60 minutes) over a predetermined period of time (e.g., 7 days), and (ii) the amount of days that a user trained beyond a minimum daily time threshold (e.g., five days) over the predetermined period of time. In such implementations, and for a given performance metric value, a user that trained more than 60 minutes over the prior seven days and more than 5 days over the last seven days would have a higher performance score than a user that trained less than 60 minutes over the last seven days or less than five days over the last seven days.

The performance metric can also be used to generate performance points (sometimes referred to herein as the "NTEL Points"). The performance points can be a percentage (e.g., 10-90%) of the performance metric, and can be displayed as a weekly tally or an all-time cumulative tally of the performance points earned. In some implementations, the performance points are earned on a predetermined point scale (e.g., 0-600 points) that accumulates over time (e.g., days, weeks, months, or years) or the course of a training session. The performance points can be compared to that of other users, and thus enable users to compete against one other. As the performance points are linked to the amount and quality of training, as well as the consistency of training over time, users are motivated to spend more time training and improving the quality of their breathing.

Other metrics generated from the input signal(s) 411 can include symmetry and coherence. The symmetry metric value can be based on the correlation between the respiration metric value and the corresponding value for the desired signal, with a better correlation corresponding to a higher symmetry metric value. The coherence metric value (e.g., an alignment or sequence metric value) can be based on a correlation between the respiration metric value (or the user's physical respiration wave) and the heart rate, or stated differently the correlation between the respiration metric value and the respiratory sinus arrythmia. In some implementations, the symmetry and coherence metric values both utilize and are generated using the shift and scale coefficients.

Figure 5:
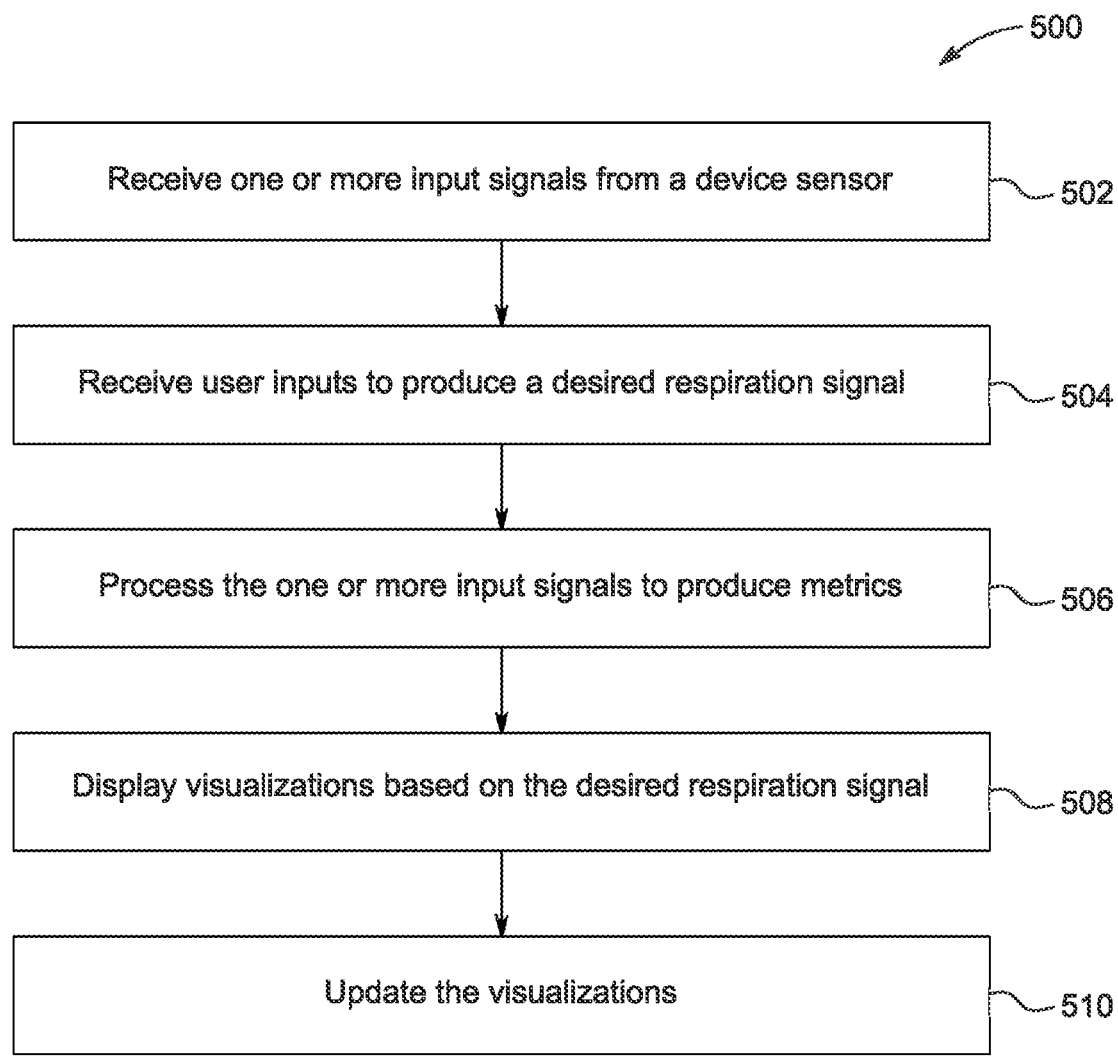
FIG. 5 is a process flow diagram of a method for processing signals received from a device sensor to generate corresponding visualizations that are continuously updated, in accordance with implementations of the present technology.

FIG. 5 is a process flow diagram of a method 500 for processing signals received from a device sensor to generate corresponding visualizations that are continuously updated, in accordance with the system. The method 500 includes receiving one or more input signals from the device sensor (process portion 502). The input signals can be the input signal(s) 411 described with reference to FIG. 4, and the sensor can be the sensor 310 described with reference to FIGS. 3A-3C or the sensor 410 described with reference to FIG. 4. As such, the input signals can be or correspond to a heart rate or R-R interval of the user, and/or an angular displacement of the sensor, which is used to generate an amount of air displaced during inhalation and/or exhalation or a relative measurement of physical movement of the abdomen area. Receiving the input signals can occur via a computing device, such as the computing device 100 described with reference to FIGS. 1 and 4. In some implementations, the sensor processes the input signals prior to sending the input signals to an external device (e.g., a mobile device or an external server).

The method 500 further comprises receiving user inputs to produce a desired signal (e.g., a desired respiration signal) (process portion 504). The user inputs can be the user inputs 406 described with reference to FIG. 4. As such, the user inputs can include user-specific data (e.g., age, weight, height, build, and/or gender), respiration settings, and/or data obtained during the training session, including breathing data corresponding to inhalation, exhalation, and hold times of the user. The user inputs can be used to generate the desired metric or data, as described herein. In some implementations, the respiration of the user is not determined based on a heart rate of the user.

The method 500 further comprises processing the one or more input signals to produce metrics (process portion 506). The metrics can be the metrics 416 described with reference to FIG. 4, and as such can include respiration volume or rate, heart rate variability (HRV) (e.g., high frequency HRV, low frequency HRV, and very low frequency HRV), consistency, performance, symmetry, and coherence. Additionally, the metrics can include a performance score and performance points. Processing of the one or more input signals can occur locally via the computing device and/or remotely via a server. The ability to process the input signals via one or both of the computing device and the server can be advantageous, as processing the input signal(s) 411 via the computing device 100 can be beneficial when wireless connection to the server or connectivity generally is unavailable, and processing the input signals via the server can improve overall processing times and enable less data to be stored locally. As described elsewhere herein, in some implementations the input signals undergo processing at the sensor, which obtained the input signal from the user, and the processed inputs signals are then provided to the mobile device and/or server for further processing.

The method 500 further comprises displaying visualizations based on the desired respiration metric and/or one or more of the metrics (process portion 508). For example, visualizations for each of the generated metrics and the desired respiration metric can be displayed via the computing device. The visualizations for multiple metrics and the desired respiration metric can be displayed simultaneously via a single plot, e.g., to enable the user to see and appreciate the opportunities for improvement in their current breathing practices. For example, a single plot can illustrate the difference between a user's current respiration metric and the idea respiration signal, as well as the performance metric, which is a function of consistency and LF percentage (or sympathetic activity). Moreover, the visualizations can be generated to utilize the shift and scale coefficients, such that the metrics and the desired respiration metric are aligned or more aligned with one another along an x-axis and y-axis of the display.

The method 500 further comprises updating the visualizations (process portion 510). The visualizations can be updated in real time on a continuous or periodic basis. In some implementations, the values displayed in the visualizations correspond to rolling average values based on data obtained over a predetermined time period (e.g., the previous 30 seconds, 1 minute, etc.). In doing so, users can monitor their breathing in real time, as well as determine whether their breathing habits, relative to the desired respiration metric, are improving over time.

FIGS. 6A-6F are illustrations of a user interface including dynamic breathing instructions provided to users, in accordance with the system. The illustrations include breathing instructions for the user that enable the system to obtain user data via a sensor and belt (e.g., the belt 305 and sensor 310 of FIGS. 3A-3C) and generate the desired respiration metric. The illustrations shown in FIGS. 6A-6F can correspond to the training session, as referred to elsewhere herein, and can last for a predetermined period of time (e.g., at least 3 minutes, 4 minutes, etc.).

Figure 6A:
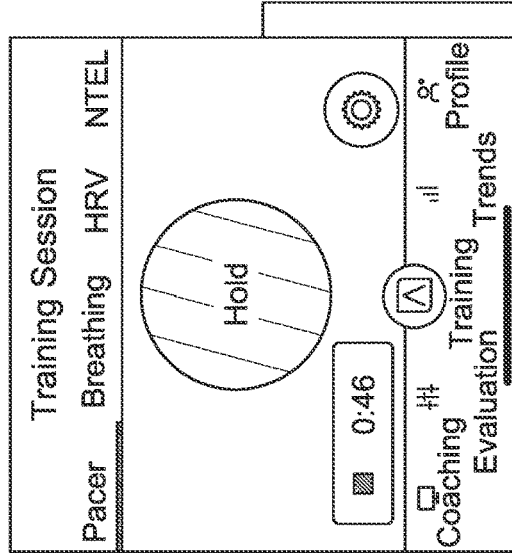
FIGS. 6A-6F are illustrations of a user interface including dynamic breathing instructions provided to users, in accordance with implementations of the present technology.
Figure 6B:
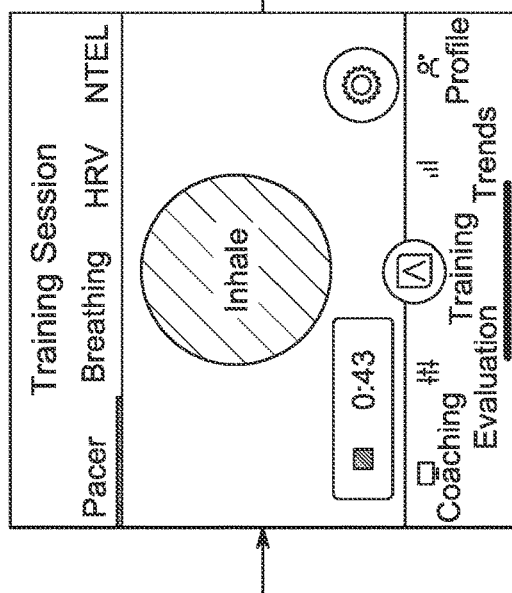
Figure 6F:
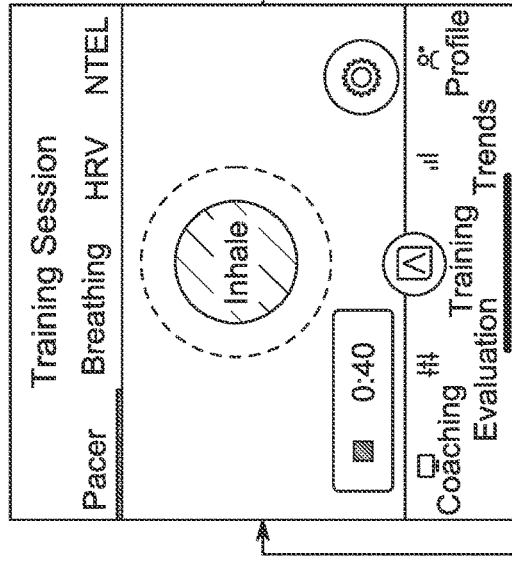
Figure 6C:
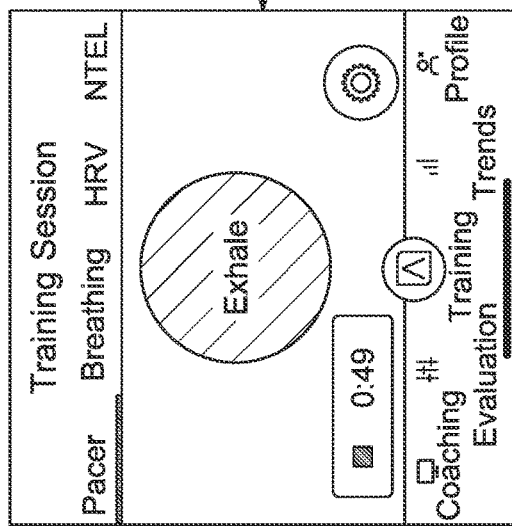
Figure 6D:
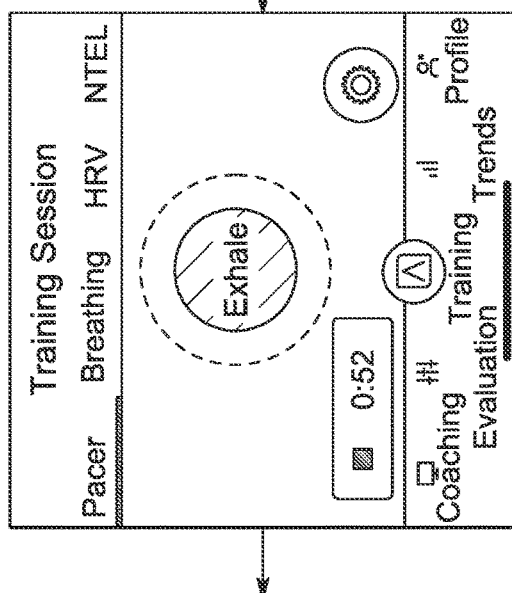
Figure 6E:
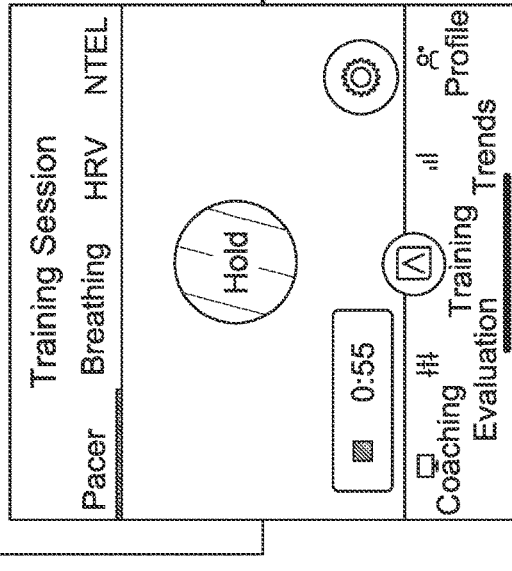

Referring first to FIG. 6A, the system instructs the user to inhale for a certain time period (e.g., 3-6 seconds). As shown in FIG. 6A, the visualization can include an inhalation visualization (e.g., a dynamic or first structure) having a first shape (e.g., circular) with a first cross-sectional dimension, and a target visualization (e.g., a static or second structure) having a second shape (e.g., circular) with a second cross-sectional dimension larger than the first cross-sectional dimension. As shown in FIG. 6B, as the user inhales, the inhalation visualization grows to fill the target visualization before transitioning to a subsequent instruction. In some embodiments, the inhalation visualization grows irrespective of the user's inhalation, and effectively instructs the user to inhale for a certain period of time (e.g., until the inhalation visualization completely fills or matches the target visualization). After inhalation, the user is instructed to hold their breath for a certain time period (e.g., 1-6 seconds, 1-4 seconds, or 3-6 seconds), as shown in FIG. 6C. Next, as shown in FIG. 6D, the user is instructed to exhale over a time period, which is typically the same as the inhalation time period. As the user exhales over the time period, the exhalation visualization decreases in size to occupy less of the outlined perimeter, as shown in FIG. 6E. At the end of the exhalation period, the user is again instructed to hold their breath, as shown in FIG. 6F, until the process repeats and the user is again asked to inhale over the time period. The overall training session can last for any predetermined period of time (e.g., at least 3 minutes, 4 minutes, etc.) or until the system has obtained enough user input data to generate a desired respiration metric.

Figure 7:
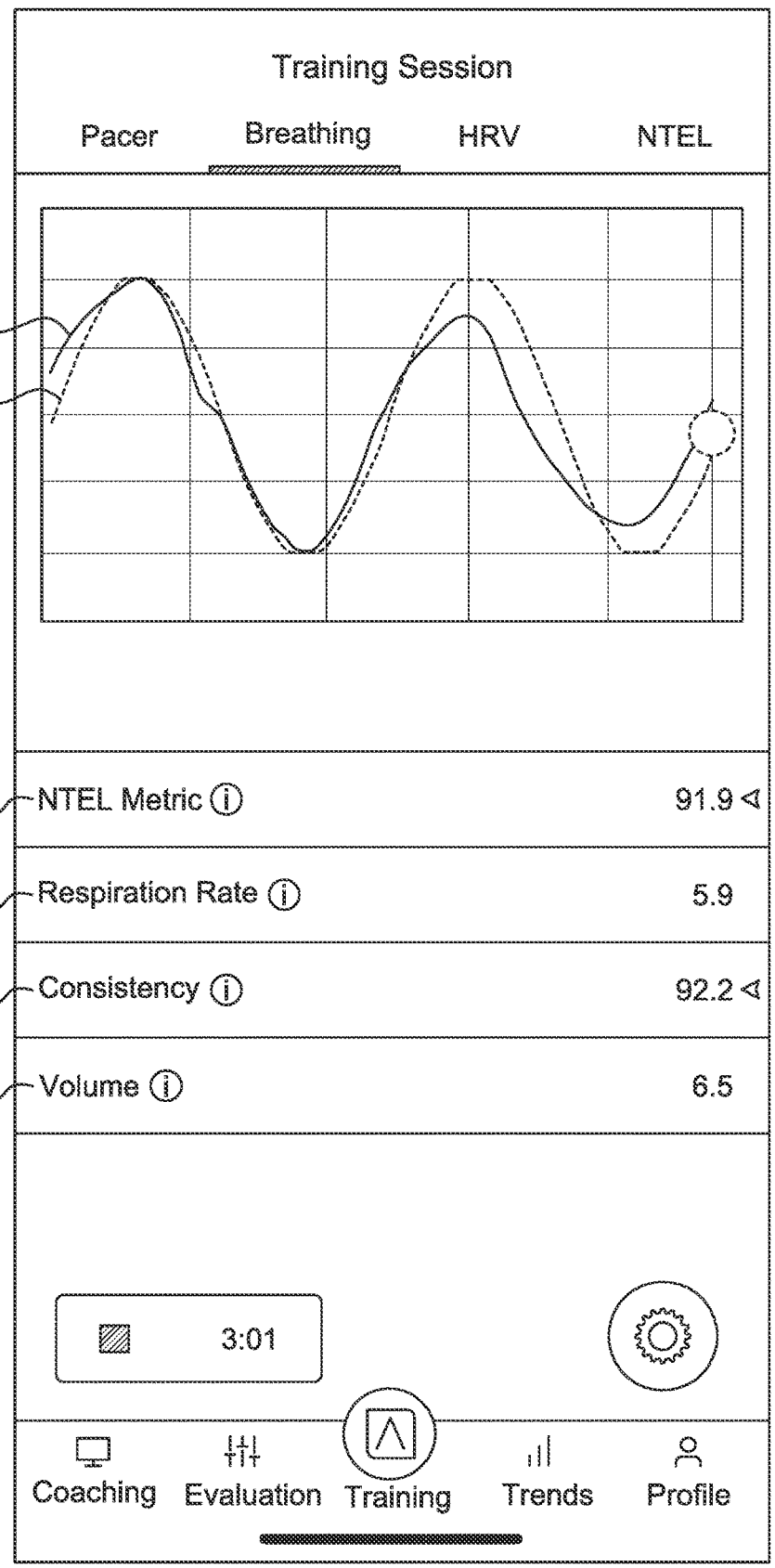
FIG. 7 is an illustration of a user interface including continuously updated breathing metrics of the user, in accordance with implementations of the present technology.

FIG. 7 is an illustration of a user interface 700 including continuously updated breathing metrics of the user, in accordance with the system. The user interface 700 includes a plot illustrating line 705 corresponding to the respiration metric (as described herein), and line 710 corresponding to the desired respiration metric (as described herein). As shown in FIG. 7, the plot illustrates the history of the lines 705, 710 over multiple breaths and shows the rise and fall associated with each breath, with the maximum value for each breath corresponding to the end of an inhalation and/or the beginning of an exhalation, and the minimum value for each breath corresponding to the end of an exhalation and/or the beginning of an inhalation. As also shown, the maximum and minimum values of the lines 705, 710 are generally aligned with one another (e.g., along the y-axis), which is in part due to the shift coefficient, as described herein. In doing so, users can visually monitor, measure, and modulate the difference between the lines 705, 710, and thus train their breathing in real-time. Also shown in FIG. 7 are values for the (i) NTEL Metric 720, (ii) the Respiration Rate 725, which corresponds to the line 710 and the respiration metric described herein, (iii) the Consistency 730 which corresponds to the consistency metric described herein, and the Volume 735 which corresponds to the line 705 and the desired respiration metric described herein. The NTEL Metric 720 and the Consistency 730 can be updated in real time and/or after training sessions.

Figure 8:
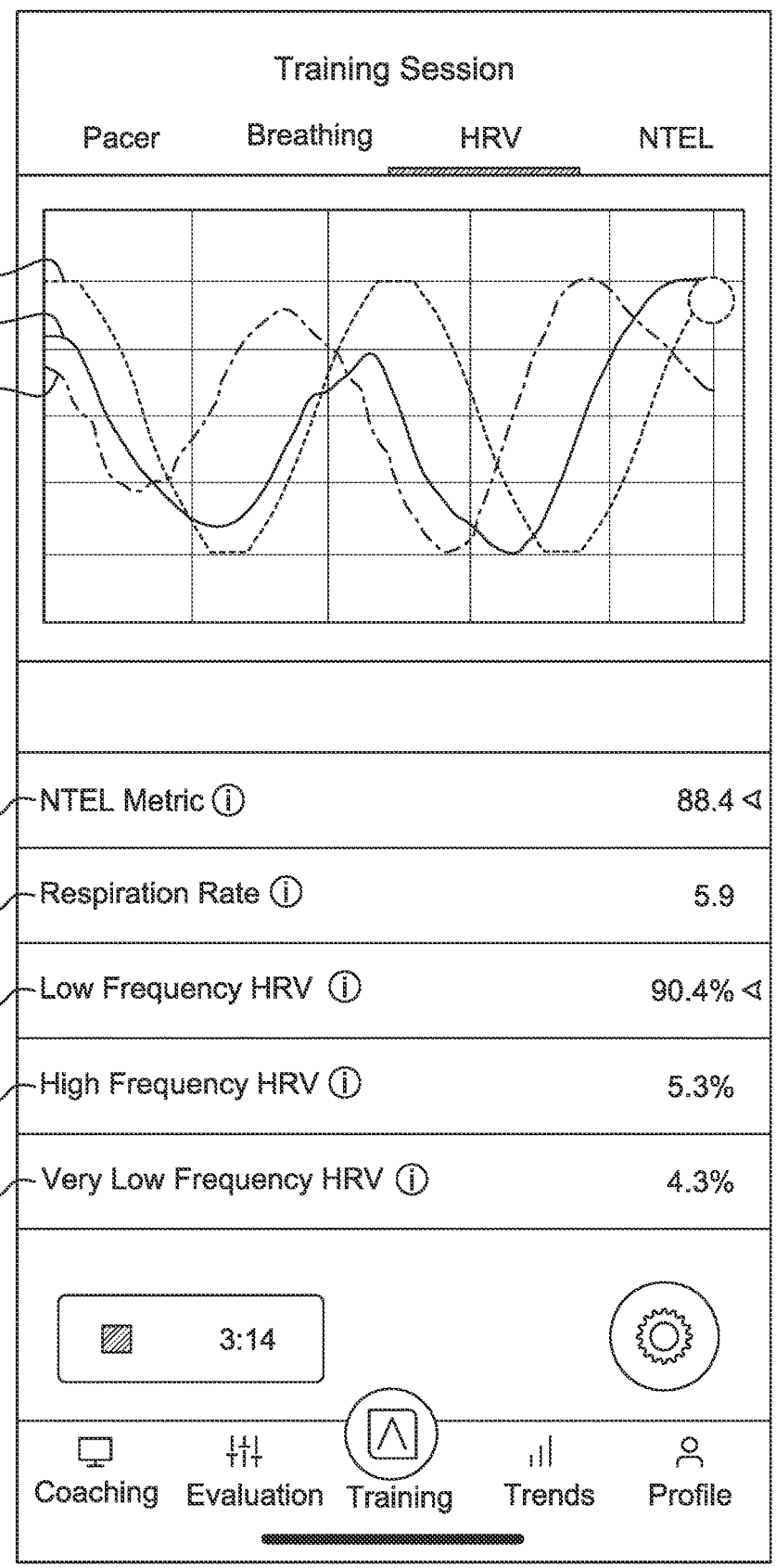
FIG. 8 is an illustration of a user interface including continuously updated heart rate variability metrics of the user, in accordance with implementations of the present technology.

FIG. 8 is an illustration of a user interface 800 including continuously updated heart rate variability metrics of the user, in accordance with the system. The user interface 800 includes many of the same features shown and described with reference to the user interface 700 of FIG. 7, including the lines 705, 710, the NTEL Metric 720, and the Respiration Rate 725. Additionally, the user interface 800 includes line 715, which is overlayed over lines 705, 710 and corresponds to the HRV metric described herein, as well as values for the Low Frequency HRV 740, High Frequency HRV 745, and Very Low Frequency HRV 4.3%.

Figure 9:
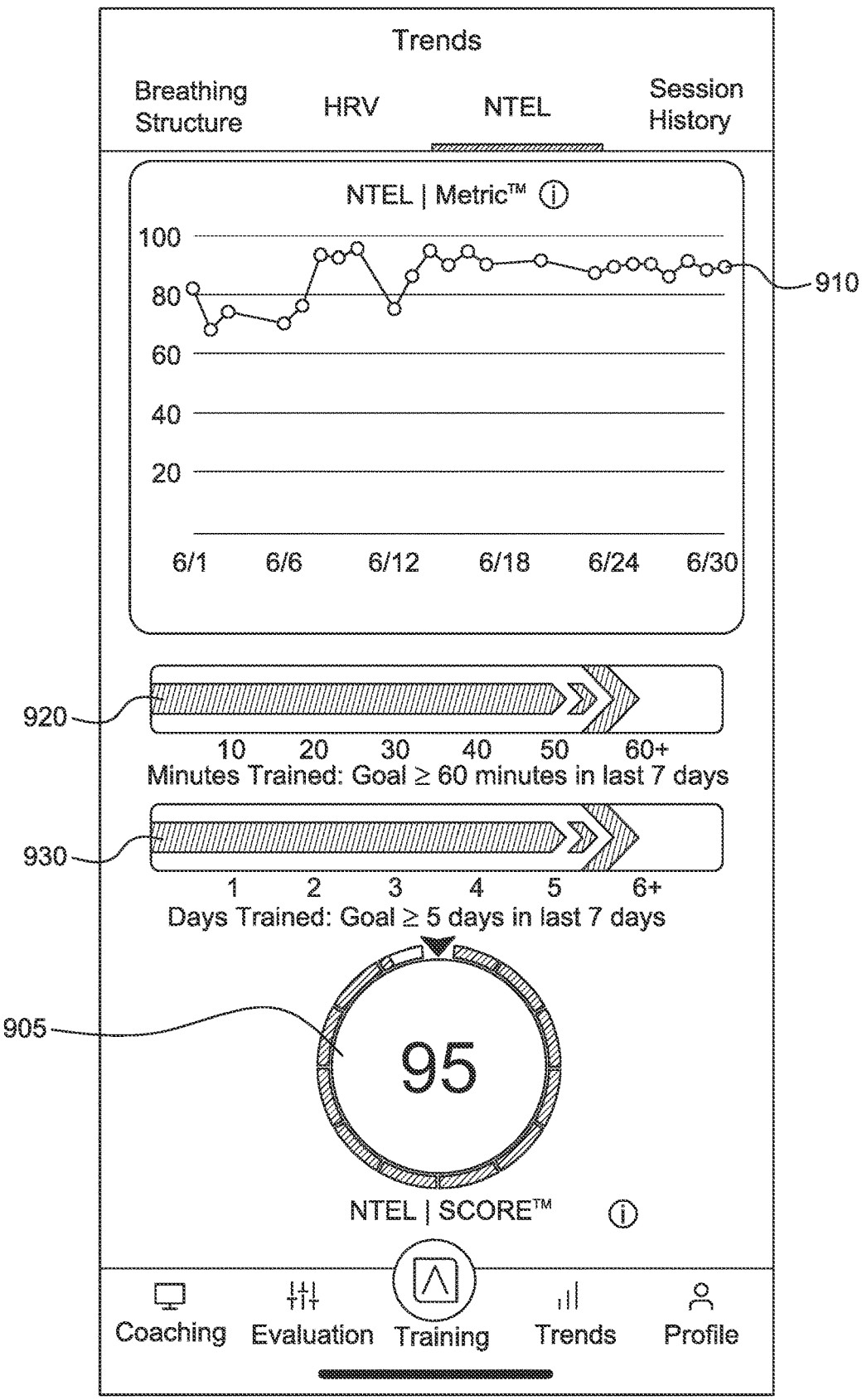
FIG. 9 is an illustration of a user interface including a continuously updated performance metric of the user, in accordance with implementations of the present technology.

FIG. 9 is an illustration of a user interface 900 including a performance metric 910 (shown as "the NTEL Metric") of the user, in accordance with the system. The performance metric 910 is based on the consistency metric and HRV metric values, as described herein (e.g., with reference to FIG. 4), and can be updated in real time and/or after training sessions. As shown in FIG. 9, the performance metric 910 is displayed in a plot so the user can monitor progress over the previous days/weeks. The performance score 905 (shown as the "NTEL Score") is displayed below the plot, and is based on the performance metric 910 and the time spent training over a previous period of time, as described with reference to FIG. 4. For example, in some implementations the performance score 905 is based equally on (i) the performance metric 910 and (ii) the time spent training over the last seven days relative to a minimum total time training threshold (e.g., 60 minutes) and a minimum daily training threshold (e.g., 5 days). In other implementations, the performance score 905 is weight most heavily (e.g., greater than 50%) by the performance metric 910. A visualization 920 for minutes trained in the last seven days and a visualization 930 for number of days trained are also shown in FIG. 9.

Figure 10:
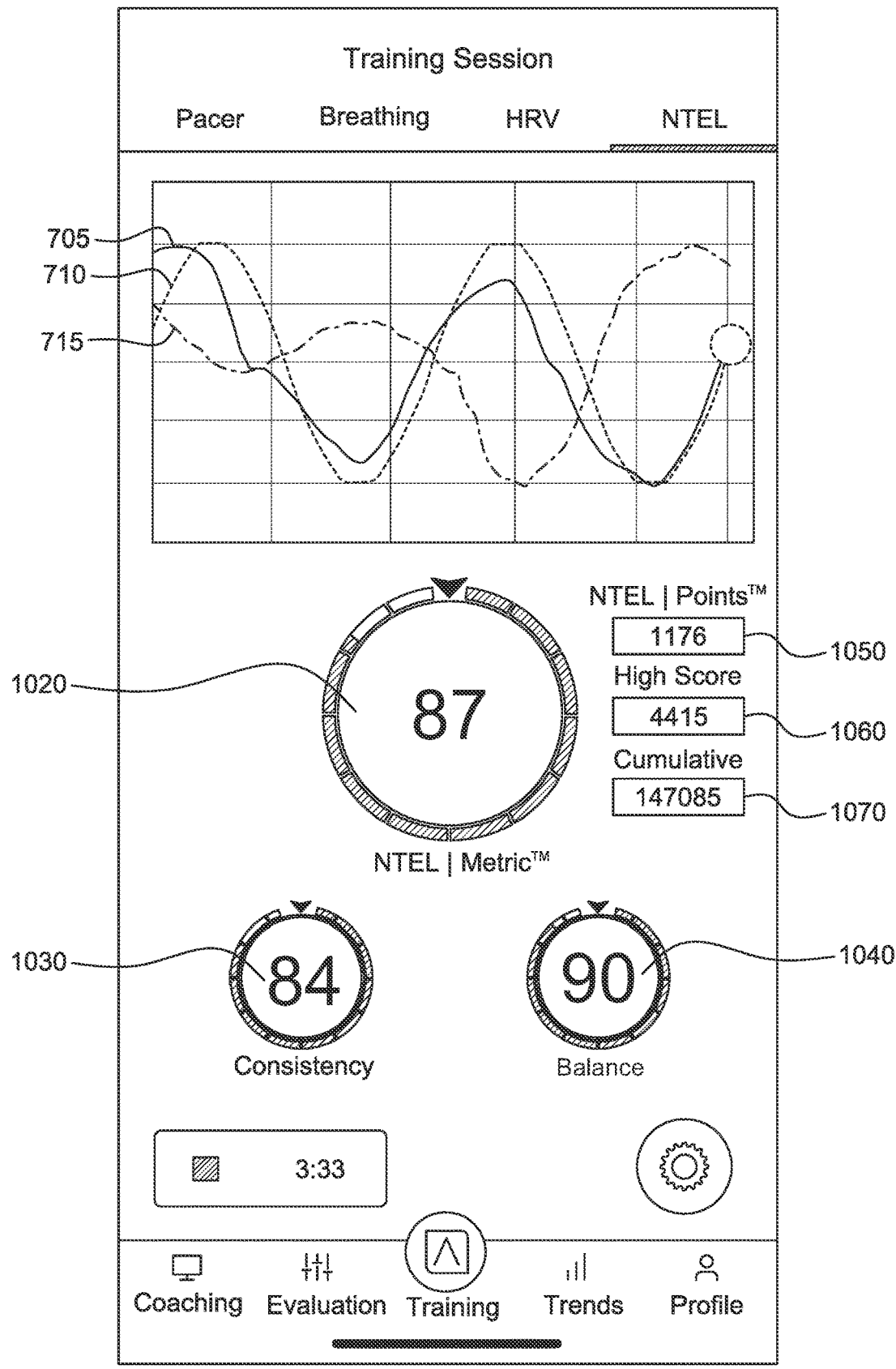
FIGS. 10 and 11 are illustrations of user interfaces including continuously updated metrics of the user, in accordance with implementations of the present technology.
Figure 11:
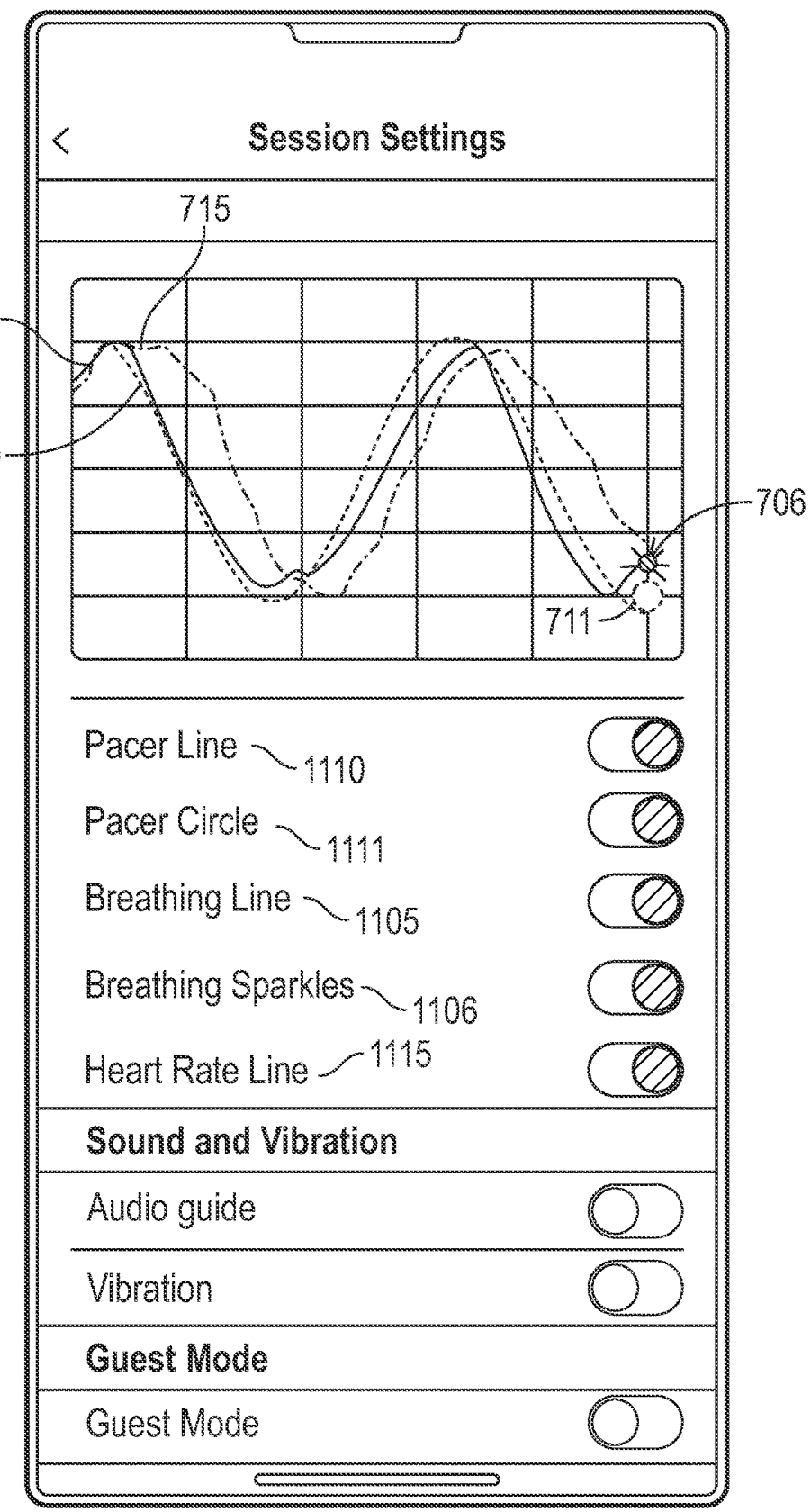

FIGS. 10 and 11 are illustrations of a user interface including continuously updated metrics of the user, in accordance with the system. Referring to FIGS. 10 and 11 together, the user interfaces include some of the visualizations and metrics previously described with reference to FIGS. 7-9, including the lines 705, 710, 715. FIG. 10 includes visualizations for a performance metric 1020 (shown as "NTEL Metric"), a consistency metric 1030, a Balance metric 1040 for HRV, a performance points metric 1050 (shown as "NTEL Points"), a weekly high score 1060 of the performance points, and a cumulative tally 1070 of the performance points, each of which is described with reference to FIG. 4. In some embodiments, certain visualizations are enhanced on the display common display to provide real time feedback if the user is performing at or above a predetermined baseline level for the user and/or a value corresponding to the visualization is within a range (e.g., 5%, 10%, 15%, 20%, etc.) of a desired value corresponding to a desired metric (as described herein) for the specific user. For example, if the performance metric 1020 is at or above a predetermined baseline NTEL Metric level for the user, the corresponding visualization becomes enhanced, e.g., by changing, blinking, and/or flashing to a unique color while the performance metric 1020 remains at or above the predetermined baseline.

FIG. 11 illustrates additional features, such as the ability to enhance one of more of the visualizations based on performance of the user. For example, when a user is performing at or above a predetermined baseline level for a particular metrics (or multiple metrics in combination) and/or a value corresponding to the visualization is within a range of a desired value corresponding to a desired metric (as described herein) for the specific user, the particular metric is enhanced to provide positive feedback to the user. In some embodiments, as shown in FIG. 11, the end of the breathing line includes an enhancement feature 706 that is enhanced or emphasized (e.g., by emitting sparkles) when the user's breath or breathing line 1105 tracks or is within a predetermined range of the pacer line 710 and/or pacer circle 711 (at the end of the pacer line 710). In doing so, the user interface is able to provide real time feedback to the user and reward the user for improvements made.

As shown in FIG. 11, the user interface also includes the ability for users to control the individual metrics that are displayed on the user interface by toggling them on or off. As such, the user has the ability to remove or undisplay a particular visualization from the common display. For example, the user interface includes a pacer line control 1110 for turning on or off display of the pacer line 710, a pacer circle control 1110 for turning on or off display of the pacer circle 711, a breathing line control 1105 for turning on or off display of the breathing line 705, an enhancement or breaking sparkles control 1106 for turning on or off display of the breathing sparkles 706, and a heart rate line control 1115 for turning on or off display of the heart rate line 705. Controlling the display of individual metrics enables a user to focus on particular aspects of their breathing training, and thus improve such aspects.

Figure 12A:
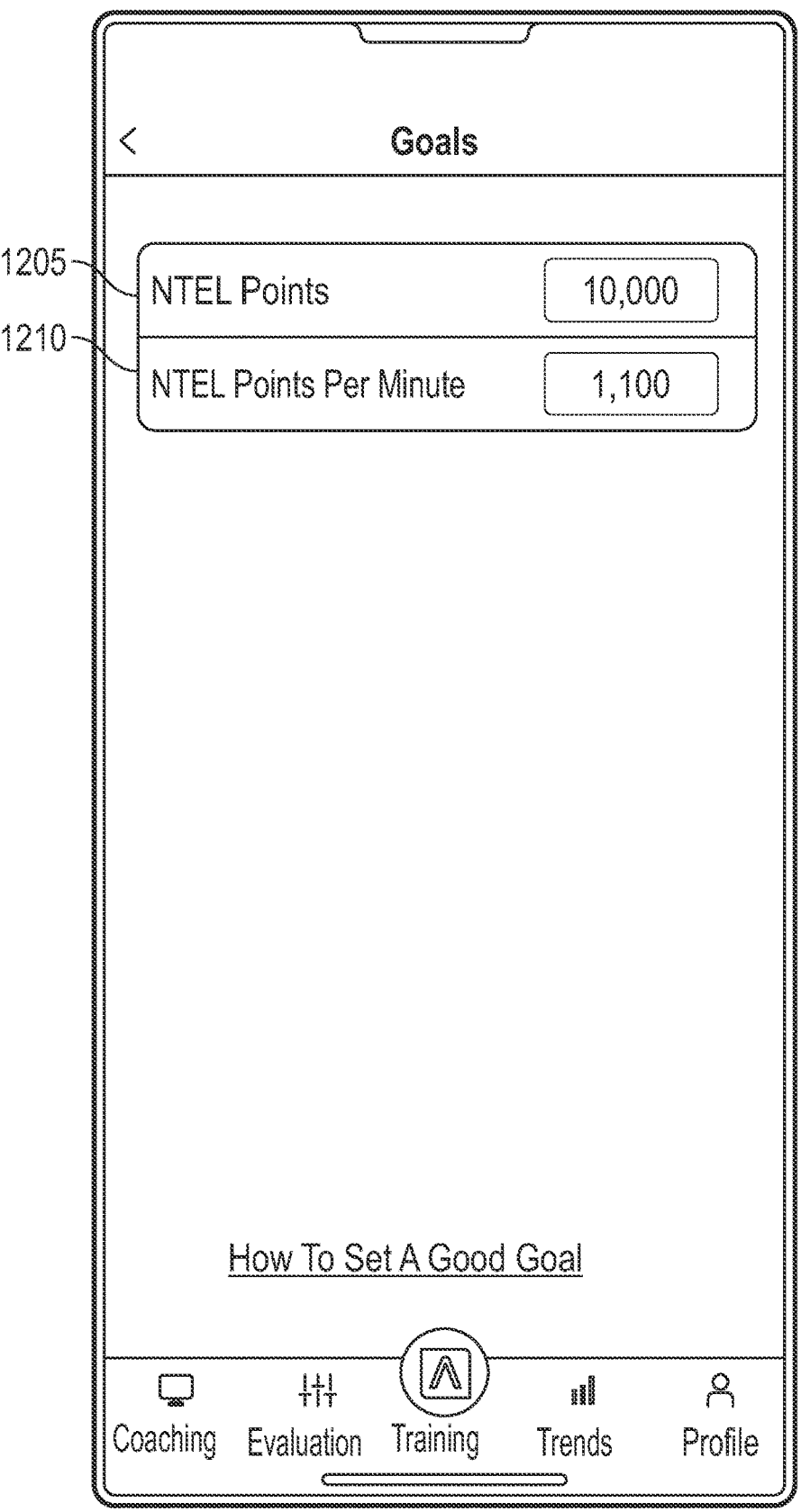
FIGS. 12A and 12B are illustrations of a user interface including continuously updated metrics with reference to goals of the user, in accordance with implementations of the present technology.
Figure 12B:
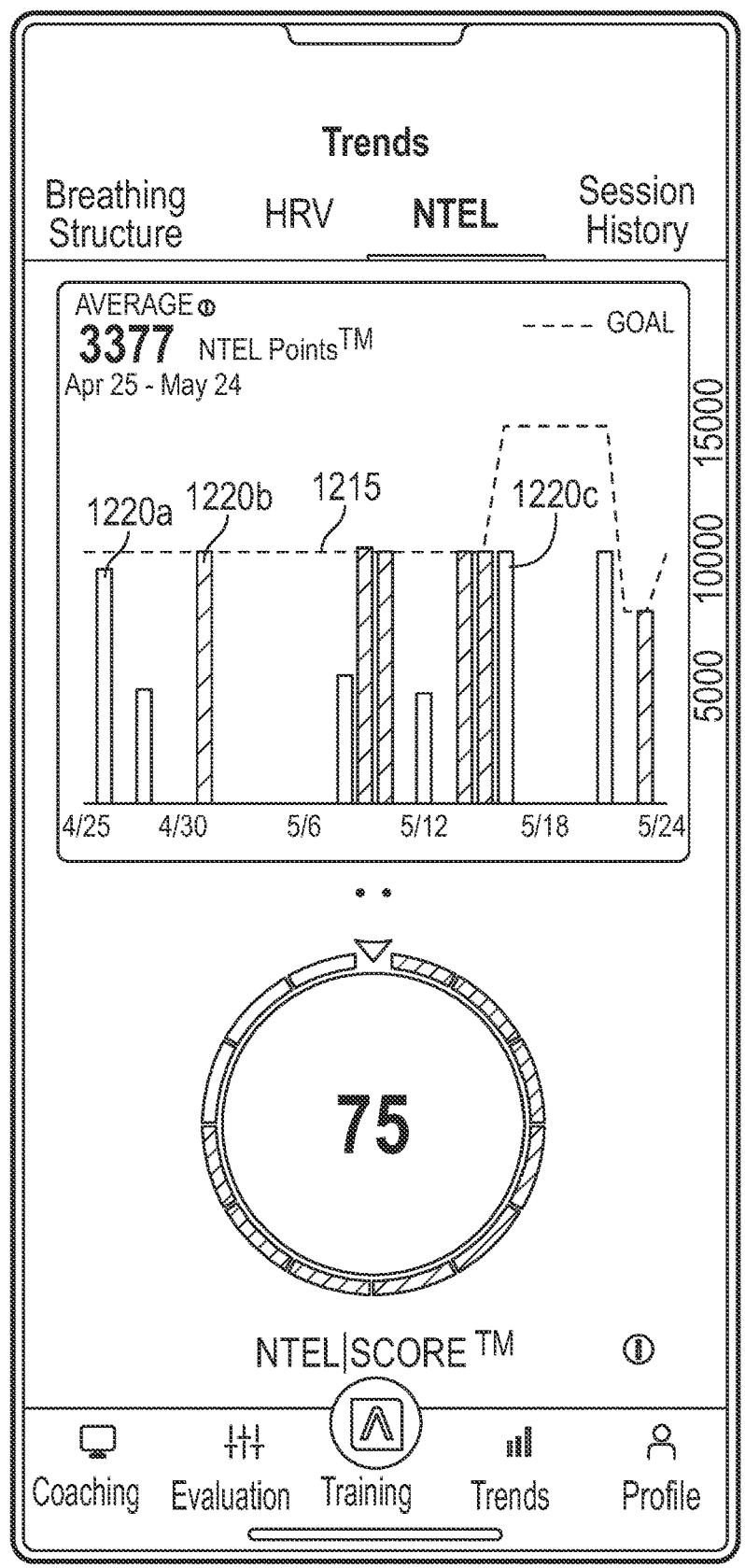

FIGS. 12A and 12B are illustrations of user interfaces including metrics with reference to goals of the user, in accordance with implementations of the present technology. FIG. 12A include an input screen for the user to enter goals, including a first input 1205 for NTEL points 1205 and a second input 1210 for NTEL Points Per Minute. FIG. 12B is an illustration including the user's NTEL Points for individual weeks over a month period. The average NTEL Points for each week, as shown via bars 1220a/b/c, are displayed in reference to the NTEL Points goal input 1205 provided by the user. When the user meets the goal for a particular week, the corresponding bar is enhanced or colored in, as shown by bar 1220b, and when the user does not meet the goal for a particular week, the corresponding bar is not enhanced or colored in, as shown by bar 1120a and 1220c. The user interface provides a visual indication that can be updated in real time, for how often the user is meeting the goals that were inputted. In doing so, the user interface provides visual cues for whether the user should update their training plan for breathing and/or their goals.

FIGS. 13A-13E are illustrations of a user interface including continuously updated metrics dynamic and breathing instructions provided to users, in accordance with implementations of the present technology. FIGS. 13A-13E illustrate a dynamic structure or visualization 1305 ("dynamic structure 1305") (e.g., the dynamic structure described with reference to FIGS. 6A-6F) providing breathing instructions to the user, a performance points metric 1320 (e.g., the performance metric 1020 or performance points metric 1050 of FIG. 10), a consistency metric 1330 (e.g., the consistency metric 1030 of FIG. 10), and a balance metric 1340 (e.g., the balance metric 1040 of FIG. 10).

Figure 13A:
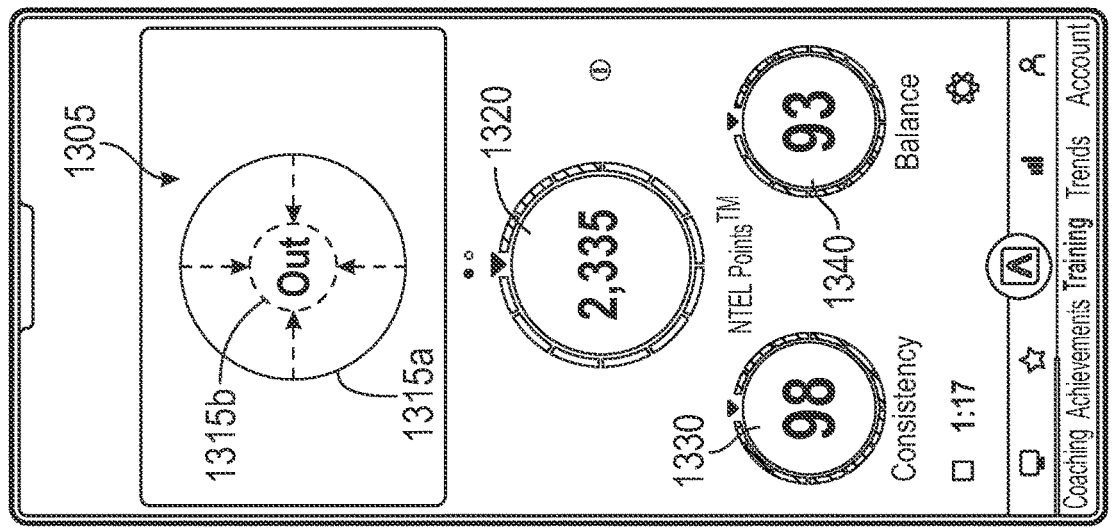
Figure 13B:
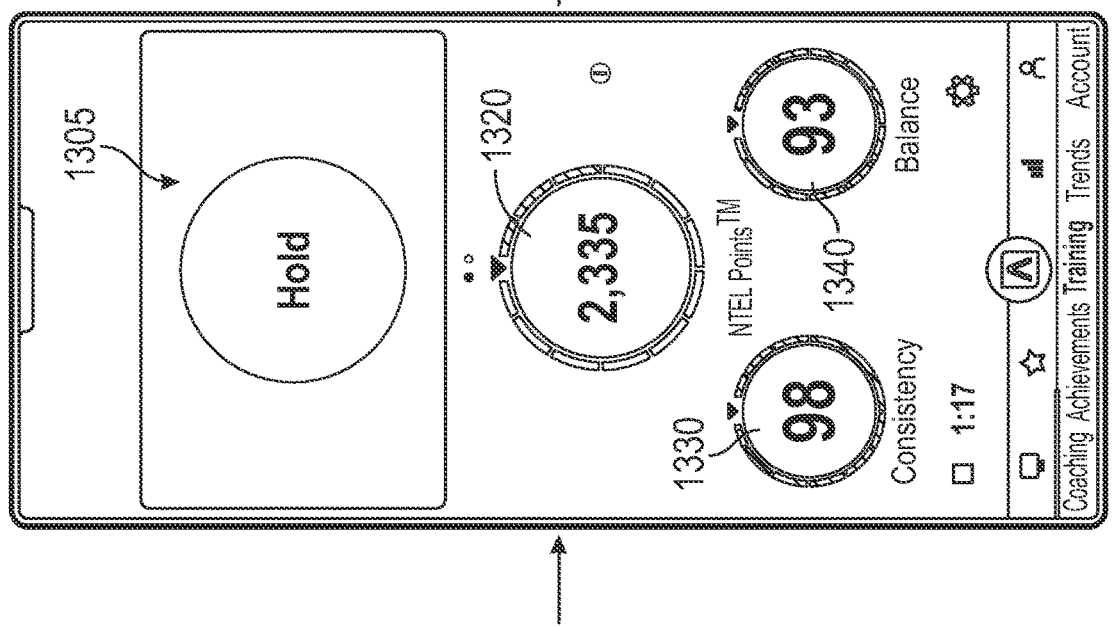
Figure 13C:
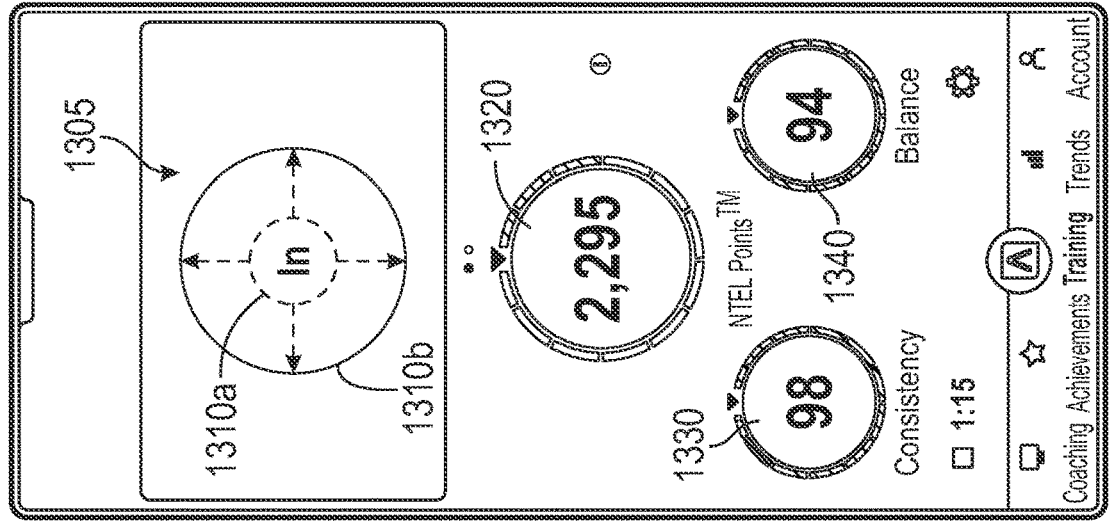

Referring first to FIG. 13A, the system instructs the user to inhale for a certain time period (e.g., 3-6 seconds) via the dynamic structure 1305. As shown in FIG. 13A, the dynamic structure 1305 has a first shape (e.g., a circular shape) with a first cross-sectional dimension (as indicated by first structure 1310a) at the beginning of the inhalation time period, and expands to a second shape (e.g., a circular shape) with a second predetermined cross-sectional dimension (as indicated by second structure 1310b) as the user inhales or breathes in. As shown in FIG. 13B, once the dynamic structure 1305 expands to assume the second predetermined cross-sectional dimension, the instruction of the dynamic structure 1305 transitions to instruct the user to hold their breath for a certain time period (e.g., 1-6 seconds, 1-4 seconds, or 3-6 seconds). During this time, the dynamic structure 1305 can remain static. As shown in FIG. 13C, once the time period for holding the breath after inhalation ends, the instruction of the dynamic structure 1305 transitions to instruct the user to exhale or blow out over a certain time period, which can be the same as the inhalation time period. As the user exhales over the time period, the dynamic structure 1305 decreases in size from a first cross-sectional dimension (as indicated by first structure 1315a) to a second predetermined cross-sectional dimension (as indicated by second structure 1315b). As shown in FIG. 13D, once the dynamic structure 1305 shrinks to assume the second predetermined cross-sectional dimension, the instruction of the dynamic structure 1305 transitions to instruct the user to hold their breath for a certain time period (e.g., 1-6 seconds, 1-4 seconds, or 3-6 seconds). As shown in FIG. 13E, once the time period for holding the breath after exhalation ends, the instruction of the dynamic structure 1305 transitions to instruct the user to again inhale, at which point the process repeats, as shown and described in FIG. 13A. The overall training session can last for any predetermined period of time (e.g., at least 3 minutes, 4 minutes, etc.) or until the system has obtained enough user input data, e.g., to generate.

As the dynamic structure 1305 is providing breathing instructions to the user, and obtaining user input data in response to the provided breathing instructions, the system can process that input data and update the corresponding metrics, including the performance points metric 1320, the consistency metric 1330, and/or the balance metric 1340, in real time or at a predetermined delay (e.g., no more than 1 second, 2 seconds, or 5 seconds). In doing so, the user receives immediate feedback as to their breathing performance.

IV. Conclusion

It will be apparent to those having skill in the art that changes may be made to the details of the above-described implementations without departing from the underlying principles of the present disclosure. In some cases, well known structures and functions have not been shown or described in detail to avoid unnecessarily obscuring the description of the implementations of the present technology. Although steps of methods may be presented herein in a particular order, alternative implementations may perform the steps in a different order. Similarly, certain aspects of the present technology disclosed in the context of particular implementations can be combined or eliminated in other implementations. Furthermore, while advantages associated with certain implementations of the present technology may have been disclosed in the context of those implementations, other implementations can also exhibit such advantages, and not all implementations need necessarily exhibit such advantages or other advantages disclosed herein to fall within the scope of the technology. Accordingly, the disclosure and associated technology can encompass other implementations not expressly shown or described herein, and the invention is not limited except as by the appended claims.

Throughout this disclosure, the singular terms "a," "an," and "the" include plural referents unless the context clearly indicates otherwise. Additionally, the term "comprising," "including," and "having" should be interpreted to mean including at least the recited feature(s) such that any greater number of the same feature and/or additional types of other features are not precluded.

Reference herein to "one embodiment," "an embodiment," "some implementations" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more implementations.

Unless otherwise indicated, all numbers expressing numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The present technology is illustrated, for example, according to various aspects described below as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.

1. A method for generating physiological metrics for display on a computing device, the method comprising:
   receiving one or more input signals from a device sensor for a user;
   receiving user inputs to produce a desired metric;
   processing the one or more input signals to produce metrics;
   displaying visualizations based on the desired metric and one or more of the metrics; and
   updating the visualizations in real time.

2. The method of the previous clause, wherein the metrics include a respiration metric and the input signals include displacement data that corresponds to inhalation and exhalation of the user, and wherein processing the one or more input signals comprises processing the displacement data to produce the respiration metric.

3. The method of any one of the previous clauses, wherein the metrics include a heart rate variability (HRV) metric and the input signals include heart rate data, and wherein processing the one or more input signals comprises processing the heart rate data to produce the HRV metric.

4. The method of clause 3, wherein processing the heart rate data includes determining a portion of the heart rate data over a predetermined period of time that corresponds to a low frequency range of 0.15-0.04 Hertz.

5. The method of claim 4, wherein the period of time is a rolling period of time, and wherein the HRV metric is continuously updated based on updated heart rate data obtained during the rolling period of time.

6. The method of clause 3, wherein processing the heart rate data comprises (i) producing buffered data over a predetermined period of time, (ii) utilizing a Fourier transform to produce power values for individual data points of the buffered data, and (iii) determining a portion of the power values that corresponds to a low frequency range of 0.15-0.04 Hertz.

7. The method of any one of the previous clauses, wherein (i) the metrics include a consistency metric based on a difference in respiration over multiple breaths and (ii) the input signals include displacement data that corresponds to inhalation and exhalation of the user, and wherein processing the one or more input signals comprises processing the displacement data to produce the consistency metric.

8. The method of any one of the previous clauses, wherein the metrics include a heart rate variability (HRV) metric and a consistency metric based on a difference in respiration over multiple breaths, wherein the input signals include heart rate data and displacement data that corresponds to inhalation and exhalation of the user, and wherein processing the one or more input signals comprises (i) processing the heart rate data to produce the HRV metric and (ii) processing the displacement data to produce the consistency metric, the method further comprising producing a performance metric based on the consistency metric and the HRV metric.

9. The method of clause 8, wherein the performance metric is based on an average of the consistency metric and the HRV metric.

10. The method of any one of the previous clauses, wherein the user inputs comprise age, weight, height, gender of the user, or any combination thereof.

11. The method of any one of the previous clauses, further comprising providing breathing instructions to the user over a training period, wherein the user inputs include displacement data obtained from the user during the training period.

12. The method of any one of the previous clauses, further comprising providing breathing instructions to the user over a training period, wherein receiving user inputs comprises receiving displacement data and shift/scale coefficients during the training period that corresponds to breathing patterns of the user, and wherein the user inputs are obtained during the training period.

13. The method of any one of the previous clauses, wherein the metrics include a respiration metric, and wherein displaying the visualizations comprises displaying the respiration metric and the desired metric simultaneously.

14. The method of any one of the previous clauses, wherein processing the one or more input signals occurs locally via a computing device without communicating with an external server.

15. The method of any one of the previous clauses, wherein processing the one or more input signals occurs via a computing device and an external server in wireless communication with the computing device.

16. The method of any one of the previous clauses, wherein displaying the visualizations comprises displaying the visualizations on a display of a computing device that processes the one or more input signals to produce the metrics.

17. The method of any one of the previous clauses, wherein displaying the visualizations comprises displaying the visualizations on a display of a computing device that does not perform processing the one or more input signals to produce the metrics.

18. The method of any one of the previous clauses, wherein displaying the visualizations comprises displaying the visualizations in real time.

19. The method of any one of the previous clauses, wherein displaying the visualizations comprises displaying the visualizations retroactively.

20. Tangible, non-transitory computer-readable media having instructions that, when executed by one or more processors, perform operations comprising:
   a) receiving one or more input signals from a device sensor for a user;
   b) receiving user inputs to produce a desired metric;
   c) processing the one or more input signals to produce metrics;
   d) displaying, on a display of a computing device, visualizations based on the desired metric and one or more of the metrics; and
   e) repeating at least operations a) and c), and updating the visualizations in real time.

21. The tangible, non-transitory computer-readable media of any one of the previous clauses, wherein the metrics include a respiration metric and the input signals include displacement data that corresponds to inhalation and exhalation of the user, and wherein processing the one or more input signals comprises processing the displacement data to produce the respiration metric.

22. The tangible, non-transitory computer-readable media of any one of the previous clauses, wherein the metrics include a heart rate variability (HRV) metric and the input signals include heart rate data, and wherein processing the one or more input signals comprises processing the heart rate data to produce the HRV metric.

23. The tangible, non-transitory computer-readable media of clause 22, wherein processing the heart rate data includes determining a portion of the heart rate data over a predetermined period of time that corresponds to a low frequency range of 0.15-0.04 Hertz.

24. The tangible, non-transitory computer-readable media of claim 23, wherein the period of time is a rolling period of time, and wherein the HRV metric is continuously updated based on updated heart rate data obtained during the rolling period of time.

25. The tangible, non-transitory computer-readable media of clause 22, wherein processing the heart rate data comprises (i) producing buffered data over a predetermined period of time, (ii) utilizing a Fourier transform to produce power values for individual data points of the buffered data, and (iii) determining a portion of the power values that corresponds to a low frequency range of 0.15-0.04 Hertz.

26. The tangible, non-transitory computer-readable media of any one of the previous clauses, wherein (i) the metrics include a consistency metric based on a difference in respiration over multiple breaths and (ii) the input signals include displacement data that corresponds to inhalation and exhalation of the user, and wherein processing the one or more input signals comprises processing the displacement data to produce the consistency metric.

27. The tangible, non-transitory computer-readable media of any one of the previous clauses, wherein the metrics include a heart rate variability (HRV) metric and a consistency metric based on a difference in respiration over multiple breaths, wherein the input signals include heart rate data and displacement data that corresponds to inhalation and exhalation of the user, and wherein processing the one or more input signals comprises (i) processing the heart rate data to produce the HRV metric and (ii) processing the displacement data to produce the consistency metric, the operations further comprising producing a performance metric based on the consistency metric and the HRV metric.

28. The tangible, non-transitory computer-readable media of clause 27, wherein the performance metric is based on an average of the consistency metric and the HRV metric.

29. The tangible, non-transitory computer-readable media of any one of the previous clauses, wherein the user inputs comprise age, weight, height, gender of the user, or any combination thereof.

30. The tangible, non-transitory computer-readable media of any one of the previous clauses, further comprising providing breathing instructions to the user over a training period, wherein the user inputs include displacement data obtained from the user during the training period.

31. The tangible, non-transitory computer-readable media of any one of the previous clauses, further comprising providing breathing instructions to the user over a training period, wherein receiving user inputs comprises receiving displacement data and shift/scale coefficients during the training period that corresponds to breathing patterns of the user, and wherein the user inputs are obtained during the training period.

32. The tangible, non-transitory computer-readable media of any one of the previous clauses, wherein the metrics include a respiration metric, and wherein displaying the visualizations comprises displaying the respiration metric and the desired metric simultaneously.

33. The tangible, non-transitory computer-readable media of any one of the previous clauses, wherein processing the one or more input signals occurs locally via a computing device without communicating with an external server.

34. The tangible, non-transitory computer-readable media of any one of the previous clauses, wherein processing the one or more input signals occurs via a computing device and an external server in wireless communication with the computing device.

35. A system for generating physiological metrics for display on a computing device, the system comprising:
  a sensor configured to obtain breathing and/or heart rate data from a user; and
  a computing device in communication with the sensor, the computing device including one or more processors, and tangible, non-transitory computer-readable media having instructions that, when executed by the one or more processors, perform operations comprising—
    receiving one or more input signals from a device sensor for a user;
    receiving user inputs to produce a desired metric;
    processing the one or more input signals to produce metrics;
    displaying, on a display of a computing device, visualizations based on the desired metric and one or more of the metrics; and
    updating the visualizations in real time.

36. The system of any one of the previous clauses, wherein the metrics include a respiration metric and the input signals include displacement data that corresponds to inhalation and exhalation of the user, and wherein processing the one or more input signals comprises processing the displacement data to produce the respiration metric.

37. The system of any one of the previous clauses, wherein the metrics include a heart rate variability (HRV) metric and the input signals include heart rate data, and wherein processing the one or more input signals comprises processing the heart rate data to produce the HRV metric.

38. The system of clause 37, wherein processing the heart rate data includes determining a portion of the heart rate data over a predetermined period of time that corresponds to a low frequency range of 0.15-0.04 Hertz.

39. The system of claim 38, wherein the period of time is a rolling period of time, and wherein the HRV metric is continuously updated based on updated heart rate data obtained during the rolling period of time.

40. The system of clause 37, wherein processing the heart rate data comprises (i) producing buffered data over a predetermined period of time, (ii) utilizing a Fourier transform to produce power values for individual data points of the buffered data, and (iii) determining a portion of the power values that corresponds to a low frequency range of 0.15-0.04 Hertz.

41. The system of any one of the previous clauses, wherein (i) the metrics include a consistency metric based on a difference in respiration over multiple breaths and (ii) the input signals include displacement data that corresponds to inhalation and exhalation of the user, and wherein processing the one or more input signals comprises processing the displacement data to produce the consistency metric.

42. The system of any one of the previous clauses, wherein the metrics include a heart rate variability (HRV) metric and a consistency metric based on a difference in respiration over multiple breaths, wherein the input signals include heart rate data and displacement data that corresponds to inhalation and exhalation of the user, and wherein processing the one or more input signals comprises (i) processing the heart rate data to produce the HRV metric and (ii) processing the displacement data to produce the consistency metric, the method further comprising producing a performance metric based on the consistency metric and the HRV metric.

43. The system of clause 42, wherein the performance metric is based on an average of the consistency metric and the HRV metric.

44. The system of any one of the previous clauses, wherein the user inputs comprise age, weight, height, gender of the user, or any combination thereof.

45. The system of any one of the previous clauses, further comprising providing breathing instructions to the user over a training period, wherein the user inputs include displacement data obtained from the user during the training period.

46. The system of any one of the previous clauses, further comprising providing breathing instructions to the user over a training period, wherein receiving user inputs comprises receiving displacement data and shift/scale coefficients during the training period that corresponds to breathing patterns of the user, and wherein the user inputs are obtained during the training period.

47. The system of any one of the previous clauses, wherein the metrics include a respiration metric, and wherein displaying the visualizations comprises displaying the respiration metric and the desired metric simultaneously.

48. The system of any one of the previous clauses, wherein processing the one or more input signals occurs locally via a computing device without communicating with an external server.

49. The system of any one of the previous clauses, wherein processing the one or more input signals occurs via a computing device and an external server in wireless communication with the computing device.

50. The system of any one of the previous clauses, wherein the sensor includes an accelerometer, a gyroscope, a strain gauge/load cell, a source of light, or any combination thereof.

51. The system of any one of the previous clauses, wherein the sensor is a first sensor configured to obtain a respiration rate, the system further comprising a second sensor in communication with the computing device and configured to obtain heart rate.

52. The system of any one of the previous clauses, wherein the sensor is configured to be worn around a chest of the user 53. A device for measuring and displaying consistency of respiration in real time, the device comprising:
  one or more processors; and
  tangible, non-transitory computer-readable media having instructions that, when executed by the one or more processors, perform the operations of any one of the previous clauses.

54. A device configured to align diaphragm-based performance breathing and Heart Rate Variability (HRV) and provide real-time feedback to a user, the device comprising:
  one or more processors; and
  tangible, non-transitory computer-readable media having instructions that, when executed by the one or more processors, perform the operations of any one of the previous clauses.

55. A system comprising:
  a chest-wearable device with a wireless transmitter and one or more transducers to generate real-time signals of a user's respiration; and
  a mobile application configured to wirelessly receive and process the real-time signals.

56. A system, comprising:
  a torso wearable device comprising:
    a wireless transmitter, and
    a sensor, coupled to the wireless transmitter, and configured to generate input signals representing respiration of a user,
      wherein, in operation, the sensor is angularly displaced in response to the respiration of the user for the generation, in real time, of the input signals; and
  at least one non-transitory computer-readable media having instructions that, when executed by a computing device in communication with the wireless transmitter, perform operations comprising:
    receiving the input signals representing respiration of the user;
    displaying a graphical user interface to the user;
    receiving one or more user inputs associated with a desired metric;
    displaying on the graphical user interface a first visualization corresponding to the desired metric; and
    displaying on the graphical user interface a second visualization corresponding to a physiological metric based on the input signals generated from the sensor, wherein the second visualization changes in real time based on real time angularly displacement of the sensor in response to the respiration of the user.

57. The system of any one of the clauses herein, wherein the operations further comprise displaying a third visualization including a first structure having a first shape and a second structure having a second shape different than the first shape, wherein, in operation, displaying the third visualization occurs while simultaneously receiving the input signals representing respiration of the user.

58. The system of any one of the clauses herein, wherein the operations further comprise displaying a third visualization including (i) a static target structure having a first cross-sectional dimension and (ii) a dynamic structure corresponding to the respiration of the user, wherein the dynamic structure has a second cross-sectional dimension different than the first cross-sectional dimension, and wherein, in operation, the second cross-sectional dimension approaches the first cross-sectional dimension as the user inhales or exhales.

59. The system of any one of the clauses herein, wherein displaying the second visualization comprises displaying the second visualization simultaneously to displaying the first visualization.

60. The system of any one of the clauses herein, wherein displaying the second visualization comprises displaying the second visualization simultaneously to displaying the first visualization, such that the first visualization and the second visualization are on a common display and the second visualization overlays the first visualization.

61. The system of any one of the clauses herein, wherein displaying the second visualization comprises:
  based on the input signals, obtaining a shift coefficient and/or a scale coefficient for the second visualization; and
  applying the shift coefficient and/or the scale coefficient to the second visualization, such that the second visualization is overlaid over the first visualization.

62. The system of any one of the clauses herein, wherein the first visualization and the second visualization are displayed on a common display having an x-axis and a y-axis, and wherein displaying the second visualization comprises:
  based on the input signals, obtaining a shift coefficient configured to adjust the second visualization along the y-axis and/or a scale coefficient configured to adjust the second visualization along the x-axis; and
  applying the shift coefficient and the scale coefficient to the second visualization, such that the second visualization is overlaid over the first visualization.

63. The system of any one of the clauses herein, wherein the input signals include data associated with multiple inhalations and exhalations of the user over time, and wherein the physiological metric includes a consistency metric indicative of a repeatability of the inhalations and exhalations over time.

64. The system of any one of the clauses herein, wherein the physiological metric is a respiration metric, and wherein displaying the second visualization comprises displaying the second visualization on a common display with the first visualization, wherein the operations further comprise:
  displaying on the common display a third visualization corresponding to a heart rate variability (HRV) of the user; and
  displaying on the common display a fourth visualization corresponding to a repeatability of the inhalations and exhalations of the user over time,
    wherein displaying the third visualization comprises overlaying the third visualization over the first visualization and the second visualization.

65. The system of any one of the clauses herein, further comprising displaying a third visualization including (i) a static shape and (ii) a dynamic shape positioned within the static shape, wherein the dynamic shape expands and contracts in response to the one or more user inputs.

66. The system of any one of the clauses herein, wherein the operations further comprise displaying a third visualization including a dynamic structure that (i) provides a breathing instruction to the user and (ii) transitions from a first cross-sectional dimension to a second cross-sectional dimension different than the first cross-sectional dimension, wherein the first cross-sectional dimension corresponds to a beginning of the breathing instruction and the second cross-sectional dimension corresponds to an end of the breathing instruction.

67. The system of any one of the clauses herein, wherein, in operation, displaying the third visualization occurs while simultaneously receiving the input signals representing respiration of the user.

68. The system of any one of the clauses herein, wherein the operations further comprise displaying a third visualization including a dynamic structure providing a first instruction, a second instruction after the first instruction, and a third instruction after the second instruction, wherein the first, second, and third instructions are associated with respiration of the user, and wherein a cross-sectional dimension of the dynamic structure changes based on the first instruction, the second instruction, and/or the third instruction.

69. A method for generating physiological metrics for display on a computing device, the method comprising:
receiving one or more input signals from a device sensor worn by a user, wherein the input signals correspond to respiration of the user;
receiving one or more user inputs indicating a desired metric;
processing the one or more input signals to produce physiological metrics based on the respiration of the user, wherein the respiration of the user is not determined based on a heart rate of the user;
concurrently displaying a first visualization and a second visualization on a common display, wherein the first visualization is based on the desired metric and the second visualization is based on at least one of the physiological metrics; and
updating the second visualization in real time based on the input signals.

70. The method of any one of the clauses herein, wherein:
the common display is on a computing device,
processing the input signals is done remotely from the computing device, and
in operation, the sensor is angularly displaced in response to the respiration of the user.

71. The method of any one of the clauses herein, wherein the physiological metrics includes a respiration metric and the input signals include displacement data that corresponds to inhalation and exhalation of the user, and wherein processing the one or more input signals comprises processing the displacement data to produce the respiration metric.

72. The method of any one of the clauses herein, wherein the physiological metrics include a heart rate variability (HRV) metric and the input signals include heart rate data, and wherein processing the one or more input signals comprises processing the heart rate data to produce the HRV metric, wherein processing the heart rate data includes determining a portion of the heart rate data over a predetermined period of time that corresponds to a low frequency range of 0.15-0.04 Hertz, and wherein the period of time is a rolling period of time, and wherein the HRV metric is continuously updated based on updated heart rate data obtained during the rolling period of time.

73. The method of any one of the clauses herein, wherein the device sensor is a strap having tilt sensor.

74. The method of any one of the clauses herein, wherein the physiological metrics include a heart rate variability (HRV) metric and the input signals include heart rate data, the method further comprising providing a graphical user interface to enable users to train their breathing in real-time, and thus improve their breathing, heart rate variability, and/or mental performance.

75. The method of any one of the clauses herein, wherein:
the physiological metrics include a heart rate variability (HRV) metric and the input signals include heart rate data,
processing the one or more input signals comprises processing the heart rate data to produce the HRV metric, and
processing the heart rate data comprises (i) producing buffered data over a predetermined period of time, (ii) utilizing a Fourier transform to produce power values for individual data points of the buffered data, and (iii) determining a portion of the power values that corresponds to a low frequency range of 0.15-0.04 Hertz.

76. At least one tangible non-transitory computer-readable medium having instructions that, when executed by one or more processors, perform operations comprising:
a) receiving heart rate data from a device sensor configured to be worn by a user and generate respiration data;
b) receiving one or more user inputs to produce a desired metric;
c) processing the heart rate data to produce physiological metrics including a heart rate variability (HRV) metric, wherein processing the heart rate data comprises utilizing a Fourier transform to produce power values for individual data points of the heart rate data;
d) displaying visualizations based on the desired metric and the HRV metrics; and
e) repeating at least operations a) and c) to update the visualizations in real time.

77. The tangible, non-transitory computer-readable medium of any one of the clauses herein, wherein displaying the visualizations comprises displaying the visualizations on a common display of a computing device, and wherein processing the one or more input signals comprises determining a portion of the heart rate data over a predetermined period of time that corresponds to a low frequency range of 0.15-0.04 Hertz.

78. The tangible, non-transitory computer-readable media of clause 74, wherein processing the heart rate data comprises producing buffered data over a predetermined period of time, and wherein utilizing the Fourier transform comprises utilizing the Fourier transform to produce power values for individual data points of the buffered data.

We claim:
1. A system, comprising:
a torso wearable device comprising:
a wireless transmitter, and
a sensor, coupled to the wireless transmitter, and configured to generate input signals representing respiration of a user,
wherein, in operation, the sensor is angularly displaced in response to the respiration of the user for the generation, in real time, of the input signals; and
at least one non-transitory computer-readable media having instructions that, when executed by a computing device in communication with the wireless transmitter, perform operations comprising:
receiving the input signals representing respiration of the user;
processing the inputs signals to produce physiological metrics including a respiration metric and a heart rate variability (HRV) metric;
displaying a graphical user interface to the user;
receiving one or more user inputs associated with a desired metric;
displaying on the graphical user interface a first visualization corresponding to the desired metric;
updating, continuously over a rolling period of time, the HRV metric and the respiration metric based on the input signals, wherein the respiration metric changes in real time based on real time angular displacement of the sensor in response to the respiration of the user;
based on the updated HRV metric, the updated respiration metric, and the input signals representing respiration of the user, displaying on the graphical user interface a dynamic score;
mapping on the graphical user interface a second visualization corresponding to the respiration metric, such that the second visualization tracks in real time the first visualization corresponding to the desired metric, wherein positioning of the second visualization relative to the first visualization indicates a breathing performance feedback to the user; and
after displaying the second visualization and based on subsequent input signals from the user, updating the mapping of the second visualization relative to the first visualization.

2. The system of claim 1, wherein mapping the second visualization comprises:
based on the input signals, obtaining a shift coefficient and/or a scale coefficient for the second visualization; and
applying the shift coefficient and/or the scale coefficient to the second visualization, such that the second visualization is overlaid over the first visualization.

3. The system of claim 1, wherein the first visualization and the second visualization are displayed on a common display having an x-axis and a y-axis, and wherein mapping the second visualization comprises:
based on the input signals, obtaining a shift coefficient configured to adjust the second visualization along the y-axis and/or a scale coefficient configured to adjust the second visualization along the x-axis; and
applying the shift coefficient and the scale coefficient to the second visualization, such that the second visualization is overlaid over the first visualization.

4. The system of claim 1, wherein the input signals include data associated with multiple inhalations and exhalations of the user over time, and wherein the physiological metrics includes a consistency metric indicative of a repeatability of the inhalations and exhalations over time.

5. The system of claim 1, wherein the operations further comprise:
displaying on the common display a third visualization corresponding to the HRV metric; and
displaying on the common display a fourth visualization corresponding to a repeatability of the inhalations and exhalations of the user over time,
wherein displaying the third visualization comprises overlaying the third visualization over the first visualization and the second visualization.

6. The system of claim 5, further comprising removing or undisplaying at least one of the first visualization, the second visualization, or the third visualization from the common display by selecting corresponding controls for displaying the first visualization, the second visualization, or the third visualization, respectively.

7. The system of claim 1, wherein the operations further comprise:
displaying on the common display a third visualization corresponding to the HRV metric, and
when a respiration value corresponding to the respiration metric is within a predetermined range of a desired value corresponding to the desired metric, enhancing the second visualization on the common display.

8. The system of claim 7, wherein enhancing the second visualization comprises causing the second visualization to flash, change color, or emit sparkles.

9. The system of claim 1, further comprising enhancing the second visualization when a physiological value corresponding to the physiological metrics is within a predetermined range of a baseline physiological value for the specific user.

10. The system of claim 9, wherein enhancing the second visualization comprises causing the second visualization to flash, change color, or emit sparkles.

11. A method for generating physiological metrics for display on a computing device, the method comprising:
receiving one or more first input signals from a device sensor worn by a user, wherein the first input signals correspond to respiration of the user;
receiving one or more user inputs indicating a desired metric;
processing the one or more input signals to produce physiological metrics based on the respiration of the user, wherein the physiological metrics include a respiration metric and a heart rate variability (HRV) metric;
updating, continuously over a rolling period of time, the HRV metric and the respiration metric, wherein the respiration metric changes in real time based on the respiration of the user; and
based on the updated HRV metric, the updated respiration metric, and the input signals, displaying on the common display a dynamic score; and
concurrently displaying on a common display a first visualization based on the desired metric and a second visualization based on the respiration metric, such that the second visualization tracks in real time the first visualization corresponding to the desired metric, wherein positioning of the second visualization relative to the first visualization indicates a breathing performance feedback to the user; and
after displaying the second visualization and based on second input signals from the user, updating the display of the second visualization relative to the first visualization.

12. The method of claim 11, wherein:
the common display is on a computing device,
processing the input signals is done remotely from the computing device, and
in operation, the sensor is angularly displaced in response to the respiration of the user.

13. The method of claim 11, wherein the first input signals include displacement data that corresponds to inhalation and exhalation of the user, and wherein processing the one or more input signals comprises processing the displacement data to produce the respiration metric.

14. The method of claim 11, wherein the first input signals include heart rate data, and wherein processing the one or more input signals comprises processing the heart rate data to produce the HRV metric, wherein processing the heart rate data includes determining a portion of the heart rate data over a predetermined period of time that corresponds to a low frequency range of 0.15-0.04 Hertz, and wherein the period of time is a rolling period of time, and wherein the HRV metric is continuously updated based on updated heart rate data obtained during the rolling period of time.

15. The method of claim 11, wherein the device sensor is a strap having tilt sensor.

16. The method of claim 11, wherein the first input signals include heart rate data, the method further comprising providing a graphical user interface to enable users to train their breathing in real-time, and thus improve their breathing, heart rate variability, and/or mental performance.

17. The method of claim 11, wherein:
the first input signals include heart rate data,
processing the one or more input signals comprises processing the heart rate data to produce the HRV metric, and
processing the heart rate data comprises (i) producing buffered data over a predetermined period of time, (ii) utilizing a Fourier transform to produce power values for individual data points of the buffered data, and (iii) determining a portion of the power values that corresponds to a low frequency range of 0.15-0.04 Hertz.

18. At least one tangible, non-transitory computer-readable medium having instructions that, when executed by one or more processors, perform operations comprising:
a) receiving heart rate data from a device sensor, wherein the device sensor is configured to be worn by a user and generate respiration data;
b) receiving one or more user inputs to produce a desired metric;
c) processing the heart rate data to produce physiological metrics including a heart rate variability (HRV) metric and a respiration metric,
wherein processing the heart rate data comprises utilizing a Fourier transform to produce power values for individual data points of the heart rate data;
d) displaying visualizations including a first visualization corresponding to the desired metric and a second visualization corresponding to the respiration metric, wherein the second visualization tracks in real time the first visualization, and wherein positioning of the second visualization relative to the first visualization indicates a breathing performance feedback to the user;
e) after displaying the second visualization, repeating at least operations a) and c) to update the second visualizations in real time relative to the first visualization; and
f) based on the HRV metric, the respiration metric, the heart rate data, and the respiration data, displaying on the graphical user interface a dynamic data indicating the performance of the user.

19. The tangible, non-transitory computer-readable medium of claim 18, wherein processing the one or more input signals comprises determining a portion of the heart rate data over a predetermined period of time that corresponds to a low frequency range of 0.15-0.04 Hertz.

20. The tangible, non-transitory computer-readable media of claim 19, wherein processing the heart rate data comprises producing buffered data over a predetermined period of time, and wherein utilizing the Fourier transform comprises utilizing the Fourier transform to produce power values for individual data points of the buffered data.

* * * * *

UNITED STATES PATENT AND TRADEMARK OFFICE
CERTIFICATE OF CORRECTION

PATENT NO. : 12,036,040 B2
APPLICATION NO. : 18/345221
DATED : July 16, 2024
INVENTOR(S) : Matthews et al.

Page 1 of 1

It is certified that error appears in the above-identified patent and that said Letters Patent is hereby corrected as shown below:

In the Specification

In Column 6, Line 38, delete "FIG." and insert -- FIGS. --.

In Column 17, Line 7, delete "claim" and insert -- clause --.

In Column 18, Line 47, delete "claim" and insert -- clause --.

In Column 20, Line 13 (Approx.), delete "claim" and insert -- clause --.

In Column 21, Line 16, delete "user" and insert -- user. --.

In Column 24, Line 49, delete "media" and insert -- medium --.

In the Claims

In Column 28, Lines 16-17, in Claim 18, delete "visualizations" and insert -- visualization --.

In Column 28, Line 28, in Claim 20, delete "media" and insert -- medium --.

Signed and Sealed this
First Day of April, 2025

Coke Morgan Stewart
*Acting Director of the United States Patent and Trademark Office*